United States Patent
Koncarevic et al.

(10) Patent No.: US 11,320,438 B2
(45) Date of Patent: May 3, 2022

(54) ISOTOPIC METHODS FOR MEASUREMENT OF TRYPTOPHAN AND METABOLITES THEREOF

(71) Applicants: ELECTROPHORETICS LIMITED, London (GB); RUPRECHT-KARLS-UNIVERSITÄT, Heidelberg (DE); DKFZ DEUTSCHES KREBSFORSCHUNGSZENTRUM, Heidelberg (DE)

(72) Inventors: Sasa Koncarevic, Sennfeld (DE); Karsten Kuhn, Hofheim am Taunus (DE); Peter Schulz-Knappe, Hemmingen (DE); Ian Hugo Pike, Tonbridge (GB); Christiane Opitz, Weinheim (DE); Michael Platten, Heidelberg (DE)

(73) Assignees: ELECTROPHORETICS LIMITED, London (GB); RUPRECHT-KARLS-UNIVERSITAT, Heidelberg (DE); DKFZ DEUTSCHES KREBSFORSCHUNGSZENTRUM, Heidelberg (DE)

( * ) Notice: Subject to any disclaimer, the term of this patent is extended or adjusted under 35 U.S.C. 154(b) by 954 days.

(21) Appl. No.: 15/772,030

(22) PCT Filed: Oct. 31, 2016

(86) PCT No.: PCT/EP2016/076265
§ 371 (c)(1),
(2) Date: Apr. 27, 2018

(87) PCT Pub. No.: WO2017/072368
PCT Pub. Date: May 4, 2017

(65) Prior Publication Data
US 2018/0246118 A1    Aug. 30, 2018

(30) Foreign Application Priority Data

Oct. 30, 2015   (GB) ................................. 1519186

(51) Int. Cl.
*G01N 33/68*    (2006.01)
*G01N 33/532*   (2006.01)

(52) U.S. Cl.
CPC ....... *G01N 33/6848* (2013.01); *G01N 33/532* (2013.01); *G01N 2458/15* (2013.01)

(58) Field of Classification Search
CPC ............. G01N 33/6848; G01N 33/532; G01N 2458/15
See application file for complete search history.

(56) References Cited

U.S. PATENT DOCUMENTS 9,023,656 B2    5/2015  Hamon et al.
2007/0023628 A1  2/2007  Hamon et al.
(Continued)

FOREIGN PATENT DOCUMENTS

CN    101568548 A    10/2009
JP    2006523305 A   10/2006
(Continued)

OTHER PUBLICATIONS

Japanese Office Action issued for JP Application No. 2018-541525, dated Nov. 4, 2020 (English translation of Pertinent Portion of Office Action attached).
(Continued)

*Primary Examiner* — Jennifer Wecker
*Assistant Examiner* — Michael Paul Shimek
(74) *Attorney, Agent, or Firm* — ArentFox Schiff LLP

(57) ABSTRACT

Tryptophan degradation is a key metabolic pathway controlling immune reactions and evidence suggests that during cancer progression generation of tryptophan metabolites
(Continued)

may be fundamental for immune escape promoting the malignant phenotype of cancer cells in an autocrine fashion. The present invention relates to methods of measuring mass tag labelled tryptophan and metabolites thereof and methods using the labelled molecules for monitoring in a subject the effectiveness of a treatment and of disease recurrence after treatment, for stratifying patients and for diagnosing suppression of an immune response in a subject.

25 Claims, 11 Drawing Sheets

Specification includes a Sequence Listing.

(56) References Cited

U.S. PATENT DOCUMENTS

| | | | |
|---|---|---|---|
| 2008/0081349 A1 | 4/2008 | Huebert et al. | |
| 2010/0029495 A1* | 2/2010 | Schaefer | G01N 33/6851 506/9 |
| 2013/0078728 A1 | 3/2013 | Li et al. | |

FOREIGN PATENT DOCUMENTS

| | | |
|---|---|---|
| JP | 2008530556 A | 8/2008 |
| JP | 2009508135 A | 2/2009 |
| JP | 2012529015 A | 11/2012 |
| JP | 2015143254 A | 8/2015 |
| WO | WO 2004/086050 A2 | 10/2004 |
| WO | 2006086540 A1 | 8/2006 |
| WO | WO 2007/031717 A1 | 3/2007 |
| WO | 2010139341 A1 | 12/2010 |
| WO | 2011036059 A1 | 3/2011 |

OTHER PUBLICATIONS

Badawy, A. A-B et al.; "Rapid Isocratic Liquid Chromatographic Separation and Quantification of Tryptophan and Six kynurenine Metabolites in Biological Samples with Ultraviolet and Fluorimetric Detection"; International Journal of Tryptophan Research 2010: 3, pp. 175-186.
Bessede, A. et al.; "Aryl hydrocarbon receptor control of a disease tolerance defense pathway"; Nature, Jul. 10, 2014; 511 (7508): pp. 184-190.
Carraro, G. et al.; "Similar sequence-free amplification of human glyceraldehyde-3-phosphate dehydrogenase for real time RT-PCR applications"; Molecular and Cellular Probes 19 (2005) pp. 181-186.
Dayon, L. et al.; "Relative Quantification of Proteins in Human Cerebrospinal Fluids by MS/MS Using 6-Plex Isobaric Tags"; Analytical Chemistry, vol. 80, No. 8, Apr. 15, 2008, pp. 2921-2931.
De Jong, W. H.A. et al.; "Plasma tryptophan, kynurenine and 3-hydroxykynurenine measurement using automated on-line solid-phase extraction HPLC-tandem mass spectrometry"; Journal of Chromatography B, 877 (2009) pp. 603-609.
GB Search Report issued for GB 1519186.9, dated Sep. 30, 2016. 5 pages.
Godin-Ethier, J. et al.; "Indoleamine 2,3-Dioxygenase Expression in Human Cancers: Clinical and Immunologic Perspectives"; Clin Cancer Res, 17(22) Nov. 15, 2011, pp. 6985-6991.
Hanahan, D. et al; "Hallmarks of Cancer: The Next Generation"; Cell, 144, Mar. 4, 2011, pp. 646-674.
Iizuka, H. et al.; "Fluorescence determination of D- and L-tryptophan concentrations in rat plasma following administration of tryptophan enantiomers using HPLC with pre-column derivatization"; Journal of Chromatography B, 879 (2011) pp. 3208-3213.
International Search Report issued for PCT/EP2016/076265, dated Jan. 30, 2017. 5 pages.
Kaspar, H. et al.; "Advances in amino acid analysis"; Anal Bioanal Chem (2009) 393: pp. 445-452.

Kuyama, H. et al.; "An approach to quantitative proteome analysis by labeling tryptophan residues"; Rapid Communications in Mass Spectrometry, 2003, 17: pp. 1642-1650.
Lesniak, W. G. et al.; "Concurrent quantification of tryptophan and its major metabolites"; Anal Biochem Dec. 15, 2013; 443(2): pp. 222-231.
Matsuo, E., et al.; "A new strategy for protein biomarker discovery utilizing 2-nitrobenzenesulfenyl (NBS) reagent and its applications to clinical samples"; Journal of Chromatography B, 877 (2009) pp. 2607-2614.
Midttun, O. et al.; "Quantitative profiling of biomarkers related to B-vitamin status, tryptophan metabolism and inflammation in human plasma by liquid chromatography/tandem mass spectrometry"; Rapid Communications in Mass Spectrometry 2009; 23: pp. 1371-1379.
Miller, C. L. et al.; "Expression of the kynurenine pathway enzyme tryptophan 2,3-dioxygenase is increased in the frontal cortex of individuals with schizophrenia"; Neurobiology of Disease 15 (2004) pp. 618-629.
Muller, A.J. et al.; "Inhibition of indoleamine 2,3-dioxygenase, an immunoregulatory target of the cancer suppression gene Bin1, potentiates cancer chemotherapy"; Nature Medicine, 2005.
Munn, D. H.; "Blocking IDO activity to enhance anti-tumor immunity"; Frontiers in Bioscience E4, Jan. 1, 2012, pp. 734-745.
Murphy, J. P. et al.; "Combining Amine Metabolomics and Quantitative Proteomics of Cancer Cells Using Derivatization with Isobaric Tags"; Anal. Chem. 2014, 86, pp. 3585-3593.
Ohashi, H. et al.; "Determination of L-trypotophan and L-kynurenine in Human Serum by using LC-MS after Derivatization with (R)-DBD-PyNCS"; International Journal of Tryptophan Research 2013:6 (Suppl. 1)9-14.
Opitz, C. A. et al.; "An endogenous tumour-promoting ligand of the human aryl hydrocarbon receptor"; Nature, 2011, 478 (7368):pp. 197-203.
Opitz, C. A. et al.; "The Indoleamine-2,3-Dioxygenase (IDO) Inhibitor 1-Methyl-D-tryptophan Upregulates IDO1 in Human Cancer Cells"; PLoS ONE; May 2011, vol. 6, Issue 5, e19823, 11 pgs.
Opitz, C. A. et al.; "Tryptophan degradation in autoimmune diseases"; Cell. Mol. Life Sci. vol. 64 (2007) pp. 2542-2563.
Ross, P. L. et al.; "Multiplexed Protein Quantitation in *Saccharomyces cerevisiae* Using Amine-reactive Isobaric Tagging Reagents"; Molecular & Cellular Proteomics, vol. 3, No. 12, 2004, pp. 1154-1169.
Sinclair, J. et al.; "Quantitative profiling of serum samples using TMT protein labelling, fractionation and LC-MS/MS"; Methods 54 (2011) pp. 361-369.
Soto, M. E. et al.; "Simultaneous determination of tryptophan, kynurenine, kynurenic and xanthurenic acids in honey by liquid chromatography with diode array, fluorescence and tandem mass spectrometry detection"; Journal of Chromatography A; 1218 (2011) pp. 7592-7600.
Steen, H. et al.; "Analysis of Bromotryptophan and Hydroxyproline Modifications by High-Resolution, High-Accuracy Precursor Ion Scanning Utilizing Fragment Ions with Mass-Deficient Mass Tags"; Analytical Chemistry, vol. 74, No. 24, Dec. 15, 2002, pp. 6230-6236.
Yamada, K. et al.; "Simultaneous measurement of tryptophan and related compounds by liquid chromatography/electrospray ionization tandem mass spectrometry"; Journal of Chromatography B, 867 (2008), pp. 57-61.
Zhu, W. et al.; "Quantitative profiling of tryptophan metabolites in serum, urine, and cell culture supernatants by liquid chromatography-tandem mass spectrometry"; Anal Bioanal Chem (2011) 401: pp. 3249-3261.
Chinese Office Action issued for CN 201680063757.2, Office Action dated Sep. 30, 2021 (English translation of Text of Third OA).
Baldi, B.G. et al.; "Stable Isotope Labeling, in Vivo, of D- and L-Tryptophan Pools in Lemna gibba and the Low Incorporation of Label into Indole-3-Acetic Acid"; Plant Physiol., vol. 95, 1991, pp. 1203-1208.
Berger, C. et al.; "Efficient Isotopic Tryptophan Labeling of Membrane Proteins by an Indole Controlled Process Conduct"; Biotechnology and Bioengineering, vol. 110, No. 6, Jun. 2013, pp. 1681-1690.

(56) References Cited

OTHER PUBLICATIONS

European Patent Office Communication pursuant to Article 94(3) issued for EP Application No. 16 790 579.3, dated Mar. 7, 2019. 4 pages.
Chinese Office Action issued for CN 201680063757.2, Office Action dated Mar. 23, 2021 (English translation of OA).
Chinese Office Action issued for CN 201680063757.2, Office Action dated Jun. 23, 2020 (English translation of OA).
Japanese Office Action issued for JP Application No. 2018-541525, dated Oct. 26, 2021 (English translation of pertinent portion of the Office Action).
India Office Action issued for India Application No. 201817019873, dated Sep. 10, 2021.

* cited by examiner

A

B

SEQUENCE LISTING

<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: PCR primer

<400> SEQUENCE: 1
cttggacctc tttggagct                                                    19

<210> SEQ ID NO 2
<211> LENGTH: 18
<212> TYPE: DNA
<213> ORGANISM: Artificial Sequence
<220> FEATURE:
<223> OTHER INFORMATION: PCR primer

<400> SEQUENCE: 2
gacctgccaa tcactgtg                                                     18

<210> SEQ ID NO 3
<211> LENGTH: 22
<212> TYPE: DNA
<213> ORGANISM: Artificial Sequence

```
<220> FEATURE:
<223> OTHER INFORMATION: PCR primer

<400> SEQUENCE: 3
ctctctgctc ctcctgttcg ac                                              22

<210> SEQ ID NO 4
<211> LENGTH: 19
<212> TYPE: DNA
<213> ORGANISM: Artificial Sequence
<220> FEATURE:
<223> OTHER INFORMATION: PCR primer

<400> SEQUENCE: 4
tgagcgatgt ggctcggct                                                  19

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
ttcagtgctt tgacgtcctg                                                 20

<210> SEQ ID NO 6
<211> LENGTH: 19
<212> TYPE: DNA
<213> ORGANISM: Artificial Sequence
<220> FEATURE:
<223> OTHER INFORMATION: PCR primer

<400> SEQUENCE: 6
tggaggaact gagcagcat                                                  19

<210> SEQ ID NO 7
<211> LENGTH: 22
<212> TYPE: DNA
<213> ORGANISM: Artificial Sequence
<220> FEATURE:
<223> OTHER INFORMATION: PCR primer

<400> SEQUENCE: 7
ggttcctcag gctatcacta cc                                              22

<210> SEQ ID NO 8
<211> LENGTH: 19
<212> TYPE: DNA
<213> ORGANISM: Artificial Sequence
<220> FEATURE:
<223> OTHER INFORMATION: PCR primer

<400> SEQUENCE: 8
cagtgtcggg gaatcaggt                                                  19

<210> SEQ ID NO 9
<211> LENGTH: 22
<212> TYPE: DNA
<213> ORGANISM: Artificial Sequence
<220> FEATURE:
<223> OTHER INFORMATION: PCR primer

<400> SEQUENCE: 9
caccctctag caatgtcaac tc                                              22
```

```
<210> SEQ ID NO 10
<211> LENGTH: 21
<212> TYPE: DNA
<213> ORGANISM: Artificial Sequence
<220> FEATURE:
<223> OTHER INFORMATION: PCR primer

<400> SEQUENCE: 10
cagactcggg atactctctc c                                              21
```

ISOTOPIC METHODS FOR MEASUREMENT OF TRYPTOPHAN AND METABOLITES THEREOF

CROSS-REFERENCE TO RELATED APPLICATIONS

This application is the U.S. National Stage Application of International Patent Application No. PCT/EP2016/076265 filed on Oct. 31, 2016, which claims priority to GB Application No. 1519186.9, filed on Oct. 30, 2015, the contents of each of which is incorporated herein by reference in its entirety.

FIELD OF THE INVENTION

The invention relates to method of measuring mass tag labelled tryptophan and metabolites thereof and methods using the labelled molecules for monitoring in a subject the effectiveness of a treatment and of disease recurrence after treatment, for stratifying patients and for diagnosing suppression of an immune response in a subject.

BACKGROUND OF THE INVENTION

The recent definition of "evading immune destruction" as an emerging hallmark of cancer reflects the increasing recognition of immune suppression and escape as critical traits of malignancy (1). In the past years tryptophan degradation has emerged as a key metabolic pathway controlling immune reactions. Emerging evidence suggests that during cancer progression generation of kynurenine by the tryptophan-catabolic enzymes indoleamine-2,3-dioxygenases (IDO) and/or tryptophan-2,3-dioxygenase (TDO) may represent a central pathway for immune escape, while also promoting the malignant phenotype of cancer cells in an autocrine fashion (2,3). While the role of TDO in cancer was just recently discovered (3), the IDO inhibitor 1-methyl-tryptophan is currently studied in clinical trials in combination with conventional chemotherapy or immunotherapy (4) based on preclinical studies in mouse models of cancer (5).

Inhibitors of IDO and TDO are being developed for the treatment of cancer and clinical trials with IDO inhibitors in solid tumors as an adjunct to chemo- or immunotherapy are currently ongoing. In addition, tryptophan degradation has been implicated in the effects of several targeted therapies. Recent evidence suggests that the tyrosine kinase inhibitor imatinib reduces IDO expression, while IDO represents a resistance mechanism against CTLA-4 blockade by ipilimumab.

While the inhibition of tryptophan degradation is studied as a means of inhibiting cancer immune escape, induction of tryptophan degradation is involved in controlling autoimmune diseases (6), excessive inflammation disease tolerance (7), chronic infection, and allergy.

As treatments modulating tryptophan degradation are becoming available, methods to efficiently and precisely measure tryptophan degradation are becoming increasingly relevant both for stratification of patients to treatments as well as assessment of therapeutic efficacy.

Measurement of tryptophan and its metabolites is routinely performed by HPLC, GC-MS or LC-MS. UV-absorption based HPLC-methods exist as well as fluorescence-based methods of specifically modified substances (11-14). Each of the methods has its specific advantages and disadvantages that are not discussed here in detail. However, when mass spectrometric methods are applied, generally higher specificity can be expected due to the measurement of exact masses with sub-ppm accuracy in addition to the LC-separation and the detection of specific fragments e.g. in the MS2 mode. Such LC-MS based methods are described for the detection of tryptophan and connected analytes (15-18). Selective reaction monitoring (SRM)-based methods have been established to enable measurement of tryptophan and several metabolites with high-sensitivity and precision using isotopically labelled standards, but also LC-ESI-MS methods based on SIM scans are described (18).

Hence, there remains a need for methods to measure tryptophan and its metabolites that may perform with superior specificity, sensitivity and throughput.

SUMMARY OF THE INVENTION

In a first aspect the present invention, therefore, provides for tryptophan and/or one or more metabolites thereof labelled with an amine-reactive mass tag that enhances signal intensity in mass spectrometry.

In one embodiment of the first aspect of the invention, tryptophan and/or one or more metabolites thereof comprise:
  i. L-tryptophan;
  ii. D-tryptophan;
  iii. 1-L-methyl-tryptophan;
  iv. 1-D-methyl tryptophan;
  v. L-kynurenine;
  vi. D-kynurenine;
  vii. 1-L-methyl-kinurenine;
  viii. 1-D-methyl-kinurenine.

The mass tag may be an isobaric tag or an isotopic mass tag. Preferably the mass tag is a dimethylpiperidine-beta-alanine derivative comprising one or more heavy isotope substitutions of hydrogen, carbon, nitrogen and/or oxygen.

In a second aspect, the invention provides for a method of measuring tryptophan and/or one or more metabolites thereof wherein the method comprises:
  a) labelling one or more test samples with one or more mass tag;
  b) labelling purified or synthetic preparations of tryptophan and/or one or more metabolites thereof with one or more additional mass tag to form a reference sample, wherein the additional mass tags are isobaric or isotopic variants of the same mass tags used in step a);
  c) mixing the one or more labelled test samples of step a) and reference sample of step b) in a predefined ratio to form one or more analytical mixtures;
  d) analysing the one or more analytical mixtures by mass spectrometry wherein the quantity of tryptophan and/or one or more metabolites thereof in the test samples is determined by comparing the signal intensity at the desired mass to charge ratio of tryptophan and/or one or more metabolites thereof with the corresponding signal intensity at the mass to charge ratio of tryptophan or its metabolite in the reference sample.

In one embodiment of this second aspect the reference sample comprises tryptophan and/or one or more metabolites thereof as defined in the first aspect of the invention and its embodiments.

In some other embodiment, the method is performed by Selected Reaction Monitoring using one or more transitions for tryptophan and/or metabolites thereof; wherein the method comprises:
  i. comparing the amount of tryptophan and/or metabolites thereof in said one or more test samples with amounts previously determined; or ii. comparing the ratios of the amounts of tryptophan to the amounts of two or more of metabolites of tryptophan in said one or more test samples;

wherein the method further comprises determining in said one or more test samples the rate and/or extent of tryptophan metabolism; wherein the transitions are preferably as defined in Table 1 and/or Table 2.

Preferably, step i) include determining the amount of tryptophan and/or metabolites thereof in said one or more test samples with known amounts of corresponding synthetic tryptophan and/or metabolites thereof which are identical to those present in said one or more test samples but have different isobaric or isotopic mass tags.

More preferably, the different mass tags are either different in structure or comprise different heavy isotope substitutions of hydrogen, carbon, nitrogen and/or oxygen.

In a third aspect, the invention provides for a method of assaying for tryptophan and/or one or more metabolites thereof, which method comprises:

a) combining a test sample, which may comprise tryptophan and/or one or more metabolites thereof, with a calibration sample comprising at least two different aliquots of tryptophan and/or one or more metabolites thereof, each aliquot of the calibration sample having a different known quantity of tryptophan and/or one or more metabolites thereof, wherein the test sample and each aliquot of the calibration sample are differentially labelled with one or more isobaric mass labels each with a mass spectrometrically distinct mass marker group, such that the test sample and each aliquot of the calibration sample can be distinguished by mass spectrometry;

b) determining by mass spectrometry the quantity of tryptophan and/or one or more metabolites thereof in the test sample and the quantity of tryptophan and/or one or more metabolites thereof in each aliquot in the calibration sample, and calibrating the quantity of tryptophan and/or one or more metabolites thereof in the test sample against the known and determined quantities of tryptophan and/or one or more metabolites thereof in the aliquots in the calibration sample.

Preferably, the tryptophan and/or one or more metabolites thereof in this third aspect of the invention comprises:
i. L-tryptophan;
ii. D-tryptophan;
iii. 1-L-methyl-tryptophan;
iv. 1-D-methyl tryptophan;
v. L-kynurenine;
vi. D-kynurenine;
vii. 1-L-methyl-kinurenine;
viii. 1-D-methyl-kinurenine.

In some embodiments of this third aspect, the test sample comprises tryptophan and one or more metabolites thereof and a calibration sample is provided for tryptophan and said one or more metabolites thereof, and step (b) is repeated for tryptophan and each of said one or more metabolites thereof.

In some other embodiments of this third aspect, the method comprises a further step prior to step (a) of differentially labelling each test sample or each aliquot of the calibration sample with one or more isobaric mass labels, and preferably the method comprises a further step of combining the differentially labelled aliquots to produce a calibration sample prior to step (a).

In a fourth aspect, the present invention provides for a method of monitoring the effectiveness of a treatment in a subject by measuring the levels of tryptophan and/or metabolites thereof according to the second and third aspects of the invention and their embodiments. Preferably, the treatment is a cancer treatment.

In a fifth aspect, the present invention provides for a method of stratifying subjects by measuring the levels of tryptophan and/or metabolites thereof according to the second and third aspects of the invention and their embodiments. Preferably, the subjects are stratified for a clinical trial.

In a sixth aspect, the present invention provides for a method of monitoring in a subject the recurrence of cancer after treatment by measuring the levels of tryptophan and/or metabolites thereof according to the second and third aspects of the invention and their embodiments. Preferably, the method is performed at intervals of 6 months, preferably at intervals of 3 months.

In a seventh aspect, the present invention provides for a method of diagnosing suppression of an immune response in a subject by measuring the levels of tryptophan and/or metabolites thereof according to the second and third aspects of the invention and their embodiments. Preferably, the suppression of the immune response is in a subject suffering from cancer.

In some embodiments of the fourth, fifth, sixth and seventh aspects of the invention the subject is a human subject.

In some embodiments of the third, fourth, fifth, sixth and seventh aspects of the invention the sample is selected from blood, plasma, serum, saliva, urine, tissue (e.g. biopsy) or combinations thereof.

In some embodiments of the second, third, fourth, fifth, sixth and seventh aspects of the invention, the mass tag or mass label is an amine-reactive mass tag or mass label that enhances signal intensity in mass spectrometry.

Furthermore, the present invention provides in an eight aspect tryptophan and/or metabolites thereof as defined in the first aspect of the invention and its embodiments for an in-vitro use of monitoring the effectiveness of a treatment in a subject, of stratifying subjects, of diagnosing suppression of an immune response in a subject, and/or of monitoring the recurrence of cancer in a subject. Alternatively, this eight aspect may be formulated as an in-vitro use of tryptophan and/or metabolites thereof as defined in any one of claims 1 to 5 for monitoring the effectiveness of a treatment in a subject, of stratifying subjects, of diagnosing suppression of an immune response in a subject, and/or of monitoring the recurrence of cancer in a subject.

Finally, in a ninth aspect the present invention provides for a kit comprising tryptophan and/or metabolites thereof as defined in the first aspect of the invention and its embodiments, wherein the kit further comprises one or more reagents to perform the methods as defined in any of the third to eight aspects of the invention and their embodiments.

DEFINITIONS

Figure 1:
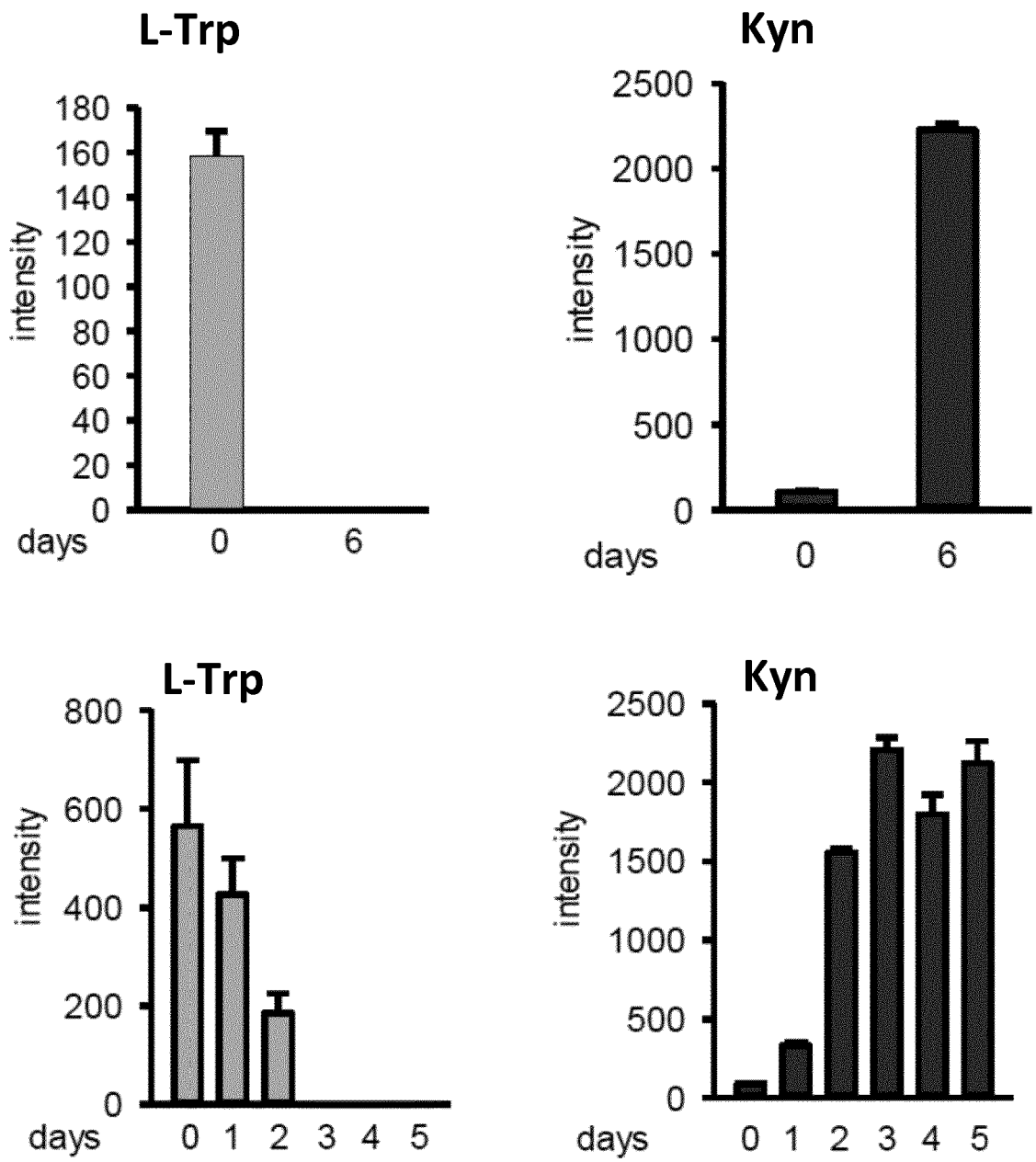
FIG. 1. Mean reporter ion intensities of three independent MS/MS reporter spectrum measurements of L-Trp (left) and Kyn (right) in cell culture media of SKOV-3 cells. The measured sample consists of six samples from three independent biological samples at different incubation times: day 0 (medium before contact with cells) and day 6 (upper panels) and days 0 to 5 (lower panels).

The term "concentration or amount" refers to the absolute or relative concentration or amount of biomarker in the sample, for example as determined by reference to a known concentration of a standard or relative to common reference standard.

The term "comparing" or "compare" or grammatical equivalents thereof, means measuring the relative concentration or amount of a biomarker in a sample relative to other samples (for example protein concentrations or amounts stored in proprietary or public databases).

The term "reference concentration or amount" refers to, but it is not limited to, protein concentrations or amounts stored in proprietary or public databases. The "reference concentration or amount" may have been obtained from a large screening of patients, or by reference to a known or previously determined correlation between such a determination and clinical information in control patients. For example, the reference values may be determined by comparison to the concentration or amount of the substance or protein in a control subject, for example a healthy person (i.e. without dementia) of similar age and gender as the subject. In addition, the reference values may have been obtained from the same subject at one or more time points which precede in time the test time point. Such earlier sample may be taken one week or more, one month or more, three months or more, most preferably six months or more before the date of the test time point.

The term "control" refers to a tissue sample or a bodily fluid sample taken from a human or non-human subject that are undiagnosed with or present no symptoms of the relevant disease. In an alternative the control may be a sample taken from the same patient prior to treatment.

The terms "selected reaction monitoring", "SRM" and "MRM" means a mass spectrometry assay whereby precursor ions of known mass-to-charge ratio representing known biomarkers are preferentially targeted for analysis by tandem mass spectrometry in an ion trap or triple quadrupole mass spectrometer. During the analysis the parent ion is fragmented and the number of daughter ions of a second predefined mass-to-charge ratio is counted. Typically, an equivalent precursor ion bearing a predefined number of stable isotope substitutions but otherwise chemically identical to the target ion is included in the method to act as a quantitative internal standard.

As used herein, the term "subject" includes any human or non-human animal. The term "non-human animal" includes all vertebrates, e.g., mammals and non-mammals, such as non-human primates, rodents, sheep, dogs, cats, horses, cows, chickens, amphibians, reptiles, etc.

The term "treat", "treating", "treatment", "prevent", "preventing" or "prevention", or grammatical equivalents thereof, includes therapeutic treatments, prophylactic treatments and applications in which one reduces the risk that a subject will develop a disorder or other risk factor. Treatment does not require the complete curing of a disorder and encompasses the reduction of the symptoms or underlying risk factors.

The term "diagnosis", or grammatical equivalents thereof, as used herein, includes the provision of any information concerning the existence or presence, non-existence or absence or probability of the disorder in a patient. It further includes the provision of information concerning the type or classification of the disorder or of symptoms which are or may be experienced in connection with it. This may include, for example, diagnosis of the severity of the disorder.

The term "efficacy" indicates the capacity for beneficial change of a given intervention (e.g. a drug, medical device, surgical procedure, etc.). If efficacy is established, that intervention is likely to be at least as good as other available interventions, to which it will have been compared. The term "efficacy" and "effectiveness" are used herein interchangeably.

The term "stratifying" or grammatical equivalents thereof indicates herein the identification of a group of subjects with shared biological characteristics individualised by using molecular, biochemical and imaging diagnostic testing. Depending on the specific characteristics used to identify the subject, stratification aims to select the optimal management for the specific group of subjects and achieve the best possible outcome in terms of risk assessment and prevention (likelihood of developing a disease) or achievement of the optimal treatment outcome (management of the disease).

The term "comprising" indicates that the subject includes all the elements listed, but may, optionally, also include additional, unnamed elements (i.e. open).

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless the context dictates otherwise, the definitions of the features/terms set out above are not limited to any particular aspect or embodiment of the invention and apply equally to all aspects and embodiments that are described herein.

DETAILED DESCRIPTION

Tryptophan degradation is a potent immunosuppressive mechanism regulating anti-tumor immune responses, autoimmune diseases and chronic infection. The inventors have employed Tandem Mass Tag® (TMT®; U.S. Pat. No. 9,023,656) reagents to measure tryptophan and its amine-containing metabolites/derivatives in a multiplex approach using tandem mass spectrometry. This method allowed simultaneous quantitative comparison of tryptophan degradation in six different samples. Application of this methodology in a cell culture model reveals degradation of the indoleamine-2,3-dioxygenase inhibitor 1-methyl-tryptophan to methyl-kynurenine. Applied to human serum samples multiplex analysis showed reduced tryptophan levels in glioblastoma patients in comparison to healthy controls demonstrating that the novel method may prove useful both in preclinical and clinical studies.

Chemical labelling of molecules with specific functional groups is used to provide increased sensitivity and chromatographic separation during the LC-MS analysis (8). Labelled molecules show a higher m/z-value and different chromatographic separation. Analytes containing amine-groups are commonly labelled with mass tags using NHS-ester chemistry. A preferred mass tag is the commercially available TMT® reagent (Life Technologies) that comprises an amine-reactive NHS-ester group, a spacer arm and a mass reporter moiety (or mass marker group). The different TMT® reagents have the same mass and structure, but contain different numbers of heavy isotopes in the mass reporter moiety. These reagents are most often used in multiplexed quantitative proteomics, whereby the attachment of a TMT®-molecule to a molecule produces the same nominal mass for labelled molecules from multiple samples. The fragmentation of the TMT®-labelled molecule produces unique reporter ions which are used for multiplexed sample quantitation. The reagents are available in various sets, which enable multiplexing rates of up to ten. TMT®-reagents were recently used for the analysis of amino acids and other metabolites by RP-HPLC-MS analysis (9). The inventors have adapted this technique to enable multiplex relative quantification of the amino acid tryptophan and its metabolites/derivatives. This allows sensitive detection and highly reproducible relative quantitation of tryptophan and its metabolites in cell culture supernatant as well as mouse and human serum samples (e.g. of time course analyses, biological replicates or multiple sample comparisons in vitro and in vivo).

The clinically studied IDO inhibitor 1-methyl-tryptophan (1-MT), a tryptophan analogue, is also amenable to multiplex analysis using amine isobaric labelling and tandem mass spectroscopy. The inventors, therefore, performed analyses not only of tryptophan metabolism but also of its most commonly used competitive inhibitor 1-MT.

The present invention provides tryptophan and/or one or more metabolites thereof labelled with an amine-reactive mass tag that enhances signal intensity in mass spectrometry. Preferably the tryptophan and/or metabolites thereof comprise:
 i. L-tryptophan;
 ii. D-tryptophan;
 iii. 1-L-methyl-tryptophan;
 iv. 1-D-methyl tryptophan;
 v. L-kynurenine;
 vi. D-kynurenine;
 vii. 1-L-methyl-kinurenine;
 viii. 1-D-methyl-kinurenine.

The mass tag may be an isobaric tag or an isotopic mass tag. Preferably the mass tag is a dimethylpiperidine-beta-alanine derivative comprising one or more heavy isotope substitutions of hydrogen, carbon, nitrogen and/or oxygen.

According to the present invention, a comparison of four tryptophan analytes, i.e. tryptophan, methyl-tryptophan, kynurenine and methyl-kynurenine, may be simultaneously explored in up to ten samples in one LC-MS run by using amino-reactive isobaric labelling reagents.

Tryptophan and/or one or more metabolites thereof may be measured by a method comprising:
 a) labelling one or more test samples with one or more mass tag;
 b) labelling purified or synthetic preparations of tryptophan and/or one or more metabolites thereof with one or more additional mass tag to form a reference sample, wherein the additional mass tags are isobaric or isotopic variants of the same mass tags used in step a);
 c) mixing the one or more labelled test samples of step a) and reference sample of step b) in a predefined ratio to form one or more analytical mixtures;
 d) analysing the one or more analytical mixtures by mass spectrometry wherein the quantity of tryptophan and/or one or more metabolites thereof in the test samples is determined by comparing the signal intensity at the desired mass to charge ratio of tryptophan and/or one or more metabolites thereof with the corresponding signal intensity at the mass to charge ratio of tryptophan or its metabolite in the reference sample.

Preferably, the reference sample comprises tryptophan and/or one or more metabolites thereof labelled with an amine-reactive mass tag that enhances signal intensity in mass spectrometry. Also preferably the tryptophan and/or metabolites thereof comprise:
  i. L-tryptophan;
  ii. D-tryptophan;
  iii. 1-L-methyl-tryptophan;
  iv. 1-D-methyl tryptophan;
  v. L-kynurenine;
  vi. D-kynurenine;
  vii. 1-L-methyl-kinurenine;
  viii. 1-D-methyl-kinurenine.

The mass tag may be an isobaric tag or an isotopic mass tag. Preferably the mass tag is a dimethylpiperidine-beta-alanine derivative comprising one or more heavy isotope substitutions of hydrogen, carbon, nitrogen and/or oxygen.

In some embodiments, the method is performed by Selected Reaction Monitoring using one or more transitions for tryptophan and/or metabolites thereof; wherein the method comprises:
  i. comparing the amount of tryptophan and/or metabolites thereof in said one or more test samples with amounts previously determined; or
  ii. comparing the ratios of the amounts of tryptophan to the amounts of two or more of metabolites of tryptophan in said one or more test samples;
  wherein the method further comprises determining in said one or more test samples the rate and/or extent of tryptophan metabolism; wherein the transitions are preferably as defined in Table 1 and/or Table 2.

Preferably, step i) include determining the amount of tryptophan and/or metabolites thereof in said one or more test samples with known amounts of corresponding synthetic tryptophan and/or metabolites thereof which are identical to those present in said one or more test samples but have different isobaric or isotopic mass tags. More preferably, the different mass tags are either different in structure or comprise different heavy isotope substitutions of hydrogen, carbon, nitrogen and/or oxygen.

This approach can be extended to other analytes of e.g. the tryptophan degradation pathway that carry amino groups (2, 35-39).

Furthermore, the method is generally also applicable for use with internal standards if absolute quantitation is desired.

Therefore, the invention provides a method of assaying for tryptophan and/or one or more metabolites thereof, which method comprises:
  a) combining a test sample, which may comprise tryptophan and/or one or more metabolites thereof, with a calibration sample comprising at least two different aliquots of tryptophan and/or one or more metabolites thereof, each aliquot of the calibration sample having a different known quantity of tryptophan and/or one or more metabolites thereof, wherein the test sample and each aliquot of the calibration sample are differentially labelled with one or more isobaric mass labels each with a mass spectrometrically distinct mass marker group, such that the test sample and each aliquot of the calibration sample can be distinguished by mass spectrometry;
  b) determining by mass spectrometry the quantity of tryptophan and/or one or more metabolites thereof in the test sample and the quantity of tryptophan and/or one or more metabolites thereof in each aliquot in the calibration sample, and calibrating the quantity of tryptophan and/or one or more metabolites thereof in the test sample against the known and determined quantities of tryptophan and/or one or more metabolites thereof in the aliquots in the calibration sample.

Preferably, the tryptophan and/or one or more metabolites thereof comprises:
  i. L-tryptophan;
  ii. D-tryptophan;
  iii. 1-L-methyl-tryptophan;
  iv. 1-D-methyl tryptophan;
  v. L-kynurenine;
  vi. D-kynurenine;
  vii. 1-L-methyl-kinurenine;
  viii. 1-D-methyl-kinurenine.

The test sample may comprise tryptophan and one or more metabolites thereof and a calibration sample may be provided for tryptophan and said one or more metabolites thereof, and step (b) is repeated for tryptophan and each of said one or more metabolites thereof.

Furthermore, the method may comprise an additional step prior to step (a) of differentially labelling each test sample or each aliquot of the calibration sample with one or more isobaric mass labels, and preferably the method may comprise a further step of combining the differentially labelled aliquots to produce a calibration sample prior to step (a).

The particular mass spectrometry platform employed is not limiting and includes but is not limited to ion trap, quadrupole, time-of-flight and orbitrap systems. Measurement of TMT®-labelled metabolites from biological samples has been successful on different mass spectrometric platforms, i.e. a QTof II (Waters) mass spectrometer coupled to an UPLC nanoLC (Waters) or on an LTQ Orbitrap Velos coupled to a Proxeon nanoLC-II and also a triple quadrupole instrument (TSQ Vantage) coupled to nanoLC. By using a semi-targeted mass spectrometric approach on the Q ToF II and the Orbitrap Velos Pro the present inventors were able not only to measure analytes expected to be present in the samples (targeted), but also to measure other analytes in a defined broader mass-range and thus, to discover that 1-MT is metabolized to methyl-kynurenine. This demonstrates one advantage of a MS method setup that is also capable of analyzing metabolites in a non-targeted fashion as used herein.

While being very time efficient, this also allows for a precise comparison of the analyzed samples, suggesting that this method may be also employed for preclinical and clinical settings. In particular, as reduced tryptophan serum concentrations have been reported in a wide variety of conditions including diverse types of cancers, inflammatory and autoimmune diseases (9, 42, 43), the method according to the invention may prove useful for stratification of patients to treatments with compounds modulating tryptophan degradation and monitoring of their efficacy.

Hence, tryptophan and/or metabolites thereof as defined herein may be used in-vitro for monitoring the effectiveness of a treatment in a subject, for stratifying subjects, for diagnosing suppression of an immune response in a subject, and/or for monitoring the recurrence of cancer in a subject.

In particular, the present invention provides for a method of monitoring the effectiveness of a treatment in a subject by measuring the levels of tryptophan and/or metabolites thereof with the methods described herein. Preferably, the treatment is a cancer treatment.

Also, the present invention provides for a method of stratifying subjects by measuring the levels of tryptophan and/or metabolites thereof with the methods described herein. In some embodiments of this aspect of the invention, the subjects are stratified for a clinical trial.

Moreover, the present invention provides for a method of monitoring in a subject the recurrence of cancer after treatment by measuring the levels of tryptophan and/or metabolites thereof with the methods described herein. The monitoring may be performed at intervals of 6 months, preferably at intervals of 3 months and most preferably at intervals of one month.

Furthermore, the present invention provides for a method of diagnosing suppression of an immune response in a subject by measuring the levels of tryptophan and/or metabolites thereof with the methods described herein. Preferably, the suppression of the immune response is in a subject suffering from cancer.

The subject of these methods is preferably a human subject; the sample may be selected from blood, plasma, serum, saliva, urine, tissue (e.g. biopsy) or combinations thereof.

The mass tag or mass label of these methods may be an amine-reactive mass tag or mass label that enhances signal intensity in mass spectrometry. In the context of this invention, the terms "mass tag" and "mass label" are interchangeable.

The present invention also provides for tryptophan and/or metabolites thereof as defined in the first aspect of the invention and its embodiments for an in-vitro use of monitoring the effectiveness of a treatment in a subject, of stratifying subjects, of diagnosing suppression of an immune response in a subject, and/or of monitoring the recurrence of cancer in a subject. Alternatively, this eight aspect may be formulated as an in-vitro use of tryptophan and/or metabolites thereof as defined in any one of claims 1 to 5 for monitoring the effectiveness of a treatment in a subject, of stratifying subjects, of diagnosing suppression of an immune response in a subject, and/or of monitoring the recurrence of cancer in a subject.

The present invention also provides for a kit comprising tryptophan and/or metabolites thereof labelled with an amine-reactive mass tag that enhances signal intensity in mass spectrometry, wherein the kit further comprises one or more reagents to perform the methods described herein.

Preferably, the kit allows for the in-vitro monitoring of the effectiveness of a treatment in a subject, in stratifying subjects, in diagnosing suppression of an immune response in a subject, and/or in monitoring the recurrence of cancer in a subject.

The reagents of the kits according to the invention may comprise any combinations of:
   a) one or more reagents for precipitating proteins in a sample;
   b) tubes, vials, containers flask or the like for handling the sample;
   c) buffers for sample preparation;
   d) amine-reactive mass tags, preferably TMT® reagents (Thermo Fisher Scientific);
   e) one or more reference samples of synthetic or purified tryptophan and/or metabolites thereof labelled with an amine-reactive mass tag;
   f) instructions to perform any of the methods described herein.

Preferably the kit comprises amine-reactive isobaric mass tags to label tryptophan and/or metabolites thereof as described herein. Preferably, the isobaric mass tags are labelled by incorporation of heavy isotopes of hydrogen, carbon, nitrogen and/or oxygen.

EXAMPLES

Certain aspects and embodiments of the invention will now be illustrated by way of example and with reference to the figures and tables described above. All documents mentioned in this specification are incorporated herein by reference in their entirety for all purposes.

Materials and Methods

Cell Culture and Reagents

SKOV-3 ovarian carcinoma cells were cultured in McCoy's 5A Medium (BioConcept, Allschwil, Switzerland) supplemented with L-Tryptophan as indicated (Sigma-Aldrich, Taufkirchen, Germany), 300 mg/l Glutamine (Carl Roth, Karlsruhe, Germany), 10% FBS (Thermo Fisher Scientific Inc., Waltham, Mass., USA) and 100 U/mL penicillin and 100 µg/mL streptomycin (PAA Laboratories, Pasching, Austria). Human embryonic kidney (HEK) cells were cultured in DMEM (PAA Laboratories), 10% FBS (Thermo Scientific) and 100 U/mL penicillin and 100 µg/mL streptomycin (PAA Laboratories). Peripheral blood mononuclear cells (PBMC) were isolated from healthy, non-related blood-donors by density-gradient centrifugation using lymphocyte separation medium LSA 1077 (PAA Laboratories) and cultured in RPMI 1640 (PAA Laboratories) containing 10% FBS (Thermo Fisher Scientific Inc) and 100 U/mL penicillin and 100 µg/mL streptomycin (PAA Laboratories). For the generation of dendritic cells (DC), CD14+ cells were separated using the magnetic activated cell sorting (MACS) technology (Miltenyi Biotec, Bergisch Gladbach, Germany) and plated in RPMI 1640 (Cambrex, Verviers, Belgium) containing 10% FBS, 200 IU/mL interleukin-4 and 1000 IU/mL GM-CSF (Immunotools, Friesoythe, Germany) for 7 days. All cells were routinely tested for contamination by the Multiplex cell Contamination Test (44). Cultures were incubated at 37° C. in a 5% CO2 atmosphere. 20 mM stock solutions (of 1-methyl-D-tryptophan (1-D-MT, lot numbers: 09315BH, 08007EJ) and 1-methyl-L-tryptophan (1-L-MT, lot numbers: 08023HE, 15399MJ) (Sigma-Aldrich) were prepared by dissolving the inhibitors in 0.1 N NaOH. The pH was adjusted to 7.5 using hydrochloric acid. To avoid contamination of the cell cultures, the stock solutions were filtered through 0.2 µm filters. Interferon-gamma (IFN-g) was purchased from Immunotools (Friesoythe, Germany).

Quantitative (q)RT-PCR

Total RNA was isolated with the Qiagen RNAeasy RNA isolation kit (Hilden, Germany) and cDNA was synthesized with the Applied Biosystems reverse-transcription-Kit (Foster City, USA) according to manufacturer's instructions. QRT-PCR was performed in an ABI 7000 thermal cycler with SYBR Green PCR Mastermix (Applied Biosystems) according to standard protocols. PCR reactions were checked by including no-RT-controls, by omission of templates and by both melting curve and gel analysis. The size of the amplicons was analyzed by loading the samples and a 100 bp ladder (Invitrogen, Leek, Netherlands) on a 2% agarose gel, which was then stained with ethidium bromide and analyzed under UV light. Standard curves were generated for each gene and the amplification was 90-100% efficient. Relative quantification of gene expression was determined by comparison of threshold values. To exclude amplification of GAPDH pseudogenes, GAPDH primer sequences were derived from Carraro et al., 2005 (25). Relative quantification of gene expression was determined by comparison of threshold values. All results were normalized to GAPDH.

```
Primer sequences were (5'-3' forward, reverse):
CYP1A1:
                                       (SEQ ID NO: 1)
CTTGGACCTCTTTGGAGCT, (SEQ ID NO: 2)
GACCTGCCAATCACTGTG GAPDH:
                                       (SEQ ID NO: 3)
CTCTCTGCTCCTCCTGTTCGAC, (SEQ ID NO: 4)
TGAGCGATGTGGCTCGGCT IDO1:
                                       (SEQ ID NO: 5)
TTCAGTGCTTTGACGTCCTG, (SEQ ID NO: 6)
TGGAGGAACTGAGCAGCAT TDO2:
                                       (SEQ ID NO: 7)
GGTTCCTCAGGCTATCACTACC;

(SEQ ID NO: 8)
CAGTGTCGGGGAATCAGGT

TIPARP:
                                       (SEQ ID NO: 9)
CACCCTCTAGCAATGTCAACTC;

(SEQ ID NO: 10)
CAGACTCGGGATACTCTCTCC
```

Overexpression of IDO and TDO in HEK Cells

The full length cDNA sequence of IDO1 and TDO was cloned via Gateway® cloning into pDEST-Flag-C, a Gateway® compatible overexpression vector containing a single C-terminal FLAG-tag, resulting in pDEST-TDO-FLAG-C and pDEST-IDO1-FLAG-C.

Basis for the pDEST-FLAG-C was the pDEST26 vector (Invitrogen). The 6×His-tag of pDEST26 was removed with site-directed mutagenesis PCR, resulting in pDEST. The single C-terminal Flag-tag was introduced into pDEST, by site-directed mutagenesis PCR, resulting in Flag-C. 2×10⁶ HEK293 cells were seeded into 6 well plates, cultured for 24 h and transfected with 2 μg of pDEST-TDO-FLAG-C, pDEST-IDO1-FLAG-C or empty control vector using FUGENE HD reagent (Roche). Cells were selected using 1.5 mg/ml neomycin (Sigma-Aldrich).

Treatment of Mice with LPS and/or 1-L-MT

Animal work was supervised by institutional animal protection officials in accordance with the National Institute of Health guidelines Guide for the Care and Use of Laboratory Animals. C57BL/6N mice were purchased from Charles River (Sulzfeld, Germany). 80 μg/mouse LPS from *S. typhi* was injected i.p. 1 mg/mouse 1-L-MT was injected i.p. 1 h before the LPS injection. After 6 h, 12 h and 24 h the mice were sacrificed and blood was drawn from their hearts. The blood was centrifuged to obtain serum, which was finally prepared for LC-MS/MS measurements.

Labelling of Pure Control Substances

L-tryptophan (Sigma-Aldrich), 1-Methyl-L-tryptophan (Sigma-Aldrich), L-kynurenine (Sigma-Aldrich), and Methyl-L-kynurenine (own synthesis, see below) were labelled for control reasons with the TMT® zero or TMT® sixplex reagent (available through Thermo Fisher Scientific). 500 μg of the substances were dissolved each in 500 μL 100 mM triethylammonium bicarbonate (TEAB, Sigma-Aldrich), then 168 μL of a 60 mM TMT® reagent stock solution in ACN LichroSolv, VWR) were added. The reaction was incubated for 1 hour at room temperature and finally quenched by adding 70 μL of 5% aqueous hydroxylamine solution (Sigma-Aldrich). Samples were dried and reconstituted in 500 μL of water:acetonitrile 95:5 with 0.1% trifluoroacetic acid for further analyses.

Synthesis of Methyl-Kynurenine

Synthesis of (S)—N-Methyl Kynurenine

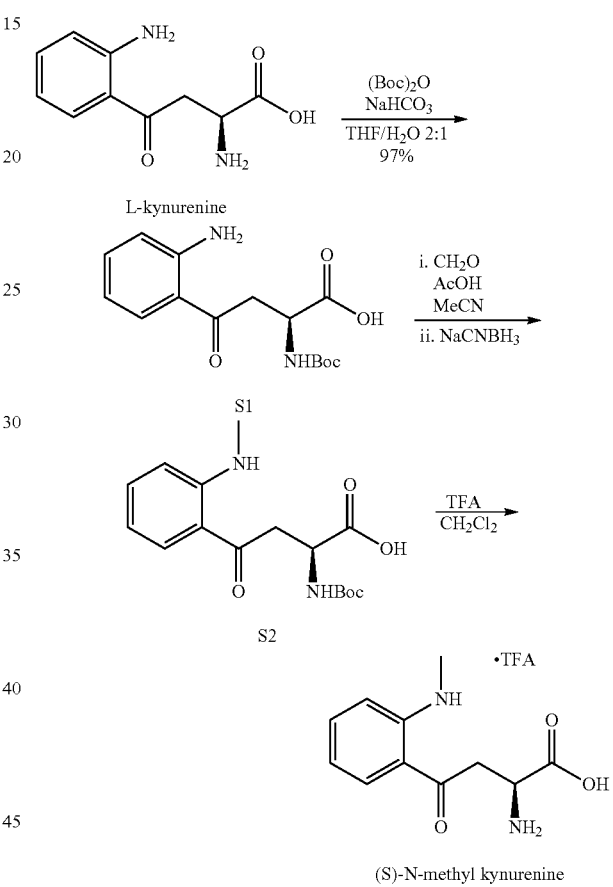

(S)-4-(2-aminophenyl)-2-((tert-butoxycarbonyl)amino)-4-oxobutanoic acid (S1): To a suspension of L-kynurenine (194 mg, 0.93 mmol) in a 2:1 THF/H₂O mixture (4 mL) was added NaHCO3 (189 mg, 1.78 mmol) and di-t-butyl dicarbonate (216 mg, 0.99 mmol) at RT. Within two minutes the reaction mixture clarified. After 2.5 h, the THF was removed with a rotary evaporator, the remaining aqueous solution was acidified with 3M HCl (5 drops) and then extracted with CH₂Cl₂ (3×5 mL). The combined organic layers were washed with brine (5 mL), dried (MgSO₄), filtered, concentrated, and the product was purified by silica gel column chromatography (10% MeOH in CH₂Cl₂) to give 279 mg (97%) of S1 as a yellow foam.

Rf 0.27 (10% MeOH in CH₂Cl₂)

LC/MS (ESI) m/z=309

(S)-2-((tert-butoxycarbonyl)amino)-4-(2-(methylamino) phenyl)-4-oxobutanoic acid (S2): To a solution of S1 (225 mg, 0.73 mmol) in acetonitrile (10 mL) was added formaldehyde (100 μL, 37% it mmol). The pH was adjusted to ~6 by the addition of acetic acid (50 μL). After 40 min at RT, NaCNBH$_3$ (162 mg, 2.58 mmol) was added. After another 90 min, the reaction mixture was diluted with H2O, basified to pH 11 with 1 M NaOH, extracted with EtOAc (3×10 mL). The combined organics were washed with brine (10 mL), dried (MgSO4), filtered, concentrated, and the product was purified by silica gel column chromatography (10% MeOH in CH$_2$Cl$_2$) to give S2 (75 mg, 32%) as a yellow foam.

Rf 0.33 (10% MeOH in CH2Cl2)

LC/MS (ESI) m/z=323

(S)—N-methyl kynurenine: To a solution of S2 (112 mg, 0.347 mmol) in CH$_2$Cl$_2$ (30 mL) was added trifluoroacetic acid (3 mL) at RT. After 90 min, the solvent was removed on a rotary evaporator. The resulting solid was dissolved in MeOH and concentrated three times in succession to remove excess TFA. The product was purified by crystallization from a mixture of EtOAc/Et2O to give (S)—N-methyl kynurenine (45 mg, 58%) as a yellow powder.

$[\alpha]D^{22}$ -44° (c 0.50, MeOH)

$^1$H NMR (400 MHz, CD$_3$OD) δ7.79 (dd, J=8.2, 1.5 Hz, 1H), 7.43 (ddd, J=8.6, 7.0, 1.5 Hz, 1H), 6.78 (d, J=8.7, 1H), 6.62 (ddd, J=8.1, 7.0, 1.1 Hz, 1H), 4.17 (dd, J=7.7, 3.3 Hz, 1H), 3.73 (dd, J=18.5, 3.3 Hz, 1H), 3.64 (dd, J=18.5, 7.7 Hz, 1H), 2.91 (s, 3H) ppm.

$^{13}$C NMR (100 MHz, CD$_3$OD) δ199.4, 172.9, 153.6, 137.0, 132.7, 117.4, 115.3, 112.6, 51.3, 39.9, 29.3 ppm.

$^{19}$F NMR (376 MHz, CD$_3$OD) δ -79.4 ppm.

LC/MS (ESI) m/z=223

TMT® Labelling of Cell Culture Supernatants

50 μL of each single cell culture supernatant was labelled with TMT® sixplex reagents (Thermo Fisher Scientific). The supernatant was diluted with 5 μL of 1M triethylammonium bicarbonate (TEAB, Sigma-Aldrich) and then 17 μL of a 60 mM TMT® reagent stock solution in ACN (LichroSolv, VWR) were added. The reaction was incubated for 1 hour at room temperature and finally quenched by adding 8 μL of 2.5% aqueous hydroxylamine solution (Sigma-Aldrich). The six samples to be compared were mixed and dried.

Sample Preparation of Mouse Serum Samples for Measurements on the Orbitrap Velos Pro 50 μL of serum sample was precipitated with 50 μL TCA-solution (60 g/l) at 4° C. overnight. The suspension was centrifuged for 15 minutes at 4° C. at 6000 g. The pellet was discarded and the supernatant used for further experiments after neutralization with 1 M NaOH to pH 7-8.

66 μL of each precipitated and neutralized mouse serum sample were diluted with 6 μL of 1M triethylammonium bicarbonate (TEAB, Sigma-Aldrich) and then 24 μL of a 60 mM TMT reagent stock solution in ACN (LichroSolv, VWR) were added. The reaction was incubated for 1 hour at room temperature and finally quenched by adding 12 μL of 2.5% aqueous hydroxylamine solution (Sigma-Aldrich). The respective six labelled serum samples to be compared were mixed and dried.

Sample Preparation of Human Serum Samples for Measurements on the TSQ Vantage System Human serum was obtained from 4 glioblastoma patients 4 age- and sex-matched healthy controls after informed consent. The serum was immediately spun down and stored at −80° C. until further analysis. The 8 human serum samples (4 sera of controls and 4 glioblastoma cases) were used to prepare two TMT® sixplex mixtures for analysis on an EASY-nLC II TSQ Vantage system (Thermo Scientific). Here, the study design comprised a reference pool mixture of the 4 sera of controls and the 4 glioblastoma cases. This reference sample consisted of equal volumes of each individual sample. Each TMT® sixplex mixture therefore contained a reference mixture, two sera from control patients and two from tumour patients—the sixth channel was left blank. Sample preparation was performed as described above. TMT®-labelled samples were mixed and dried.

Reversed Phase Purification of the Mixed Samples

The dry TMT® sixplex mixtures were reconstituted in 300 μL of water:acetonitrile 95:5 with 0.1% trifluoroacetic acid (buffer A). 150 μL were fractionated by reversed phase chromatography (Nucleosil 120-5 C18 column, 250 mm×4.6 mm, Macherey Nagel) using a Waters 2695 HPLC with UV detection at 214 nm. After loading, the sample was washed 4 min with buffer A. Then, the substances were eluted by increasing the acetonitrile content within 40 min to 55%. The flow rate was kept at 1.5 mL/min over the entire gradient. The fraction from 18-30 minutes was collected and dried.

Mass Spectrometric Measurement of Cell Culture Supernatant and Serum Samples

Samples were either measured on a QTof II (Waters) mass spectrometer coupled to an UPLC nanoLC (Waters) on an LTQ Orbitrap Velos Pro (Thermo Scientific) coupled to a Proxeon nanoLC-II (Thermo Scientific) or a triple quadrupole system coupled to nanoLC-II (EASY-nLC II TSQ Vantage system). The samples were resolved in 150 μl 2% ACN, 0.1% formic acid (1 μL sample=1 μL mixed supernatant equivalent).

For the QTof MS runs, the cell supernatant sample mixtures were diluted 1:20 in 2% ACN and 0.1% formic acid and 3 μl were injected for LC-MS/MS analysis.

For the Orbitrap MS runs, cell supernatant sample mixtures were diluted 1:100 in 2% ACN and 0.1% formic acid and 2 μl were applied for LC-MS/MS analysis (~0.02 μl mixed sample).

For the Orbitrap MS runs the mixed mouse serum sample was dissolved in 2% ACN, 0.1% formic acid and ~0.88 μL of mixed serum equivalent was loaded on column. For LC separation, a 25 minutes gradient was used to separate the analytes of choice (15% to 30% ACN). The prepared human serum sample mixtures were solved in 2% ACN, 0.1% formic acid and 1 μl mixed serum equivalent used per MS-run.

For MS analysis on the QTof, survey full-scan MS spectra (m/z 350-500) were acquired with a scan time of 1000 ms and inter-scan delay of 100 ms. Each full scan was followed by the selection of the two most intense ions for collision induced dissociation (CID)-MS/MS analysis with a scan time of 2000 ms and an inter-scan delay of 100 ms. Only singly charged precursors were selected for further MS/MS acquisition. MS/MS was triggered data-dependent for m/z 434.27; 438.27; 448.27; 452.27 (±500 mDa).

For high resolution MS analysis on the Orbitrap, a selected ion monitoring (SIM) Top10 HCD (high-collision dissociation) method was used to monitor the analytes of choice.

The SIM m/z range was from 350-500 Th with a resolution of 60000 and an AGC setting of 5e4 with a maximum scan time of 500 ms. MS/MS was acquired as TOP10 in HCD mode with a resolution of 7500 and an AGC setting of 5e4 with a maximum scan time of 500 ms. Isolation width was 1.5 amu and normalized collision energy was 60. The default charge state of the precursor was set to z=1. All other charge states were rejected. Analytes of interest were acquired in MSMS mode using an inclusion list only mode (±50 ppm) and all other analytes not included in the list were discarded. Analytes were then identified by their m/z, retention time and typical fragments and their TMT® sixplex reporter intensities exported using an in-house adapted version of MZmine. The inclusion list contained the calculated masses of the four analytes tryptophan, methyl-tryptophan, kynurenine and methyl-kynurenine being labelled with TMT® sixplex-reagents.

Extracted ion chromatograms were visualized using either MassLynx 4.1 (Waters) for QTof data or Xcalibur2.1 (Thermo Scientific) for Orbitrap data and reporter ion intensities as well as product ions were exported from accumulated MS/MS spectra of the corresponding analytes.

For MS analysis on a Triple Quadrupole TSQ Vantage system the two TMT® sixplex mixtures of human serum samples were resuspended in 150 µL 2% ACN/0.1% FA, diluted 1:20 and 2 µL (0.1 µL serum equivalent) injected into an EASY-nLC II TSQ Vantage system (Thermo Scientific).

First samples were loaded on a 2 cm long (OD 360 µm, ID 100 µm) capillary column filled with 5 µm ReproSil-Pur C18-AQ (Dr. Maisch GmbH) for trapping and clean-up. Then, analytes were separated through a 15 cm long (OD 360 µm, ID 75 µm) capillary column filled with 3 µm ReproSil-Pur C18-AQ (Dr. Maisch GmbH) using a 25 minutes gradient from 15 to 30% acetonitrile in 0.1% FA at 300 nL/min.

Eluting analytes were ionized by nano electrospray at 1.6 kV. The Triple Quadrupole instrument was operated in positive and SRM mode. Capillary temperature was set to 220° C. Transition parameters were as stated in Table 1 and Table 2 for tryptophan and kynurenine, respectively. Transition scan time was calculated at 24 ms. Peak scan width (FWHM) for Q1 and Q3 were set to 0.5 and 0.7, respectively. Collision gas pressure was set to 1.8 mTorr, chromfilter peak width to 6.0 s and declustering voltage to 5 V.

TABLE 1

Transition parameters for tryptophan

| Analyte | Parent | Product | CE | S-lens |
|---|---|---|---|---|
| TMT® 126 | 434.26 | 126.13 | 29 | 172 |
| TMT® 127 | 434.26 | 127.13 | 29 | 172 |
| TMT® 128 | 434.26 | 128.13 | 29 | 172 |
| TMT® 129 | 434.26 | 129.14 | 29 | 172 |
| TMT® 130 | 434.26 | 130.14 | 29 | 172 |
| TMT® 131 | 434.26 | 131.14 | 29 | 172 |
| Fragment 188 | 434.26 | 188.07 | 28 | 172 |

TABLE 2

Transition parameters for kynurenine

| Analyte | Parent | Product | CE | S-lens |
|---|---|---|---|---|
| TMT® 126 | 438.25 | 126.13 | 35 | 173 |
| TMT® 127 | 438.25 | 127.13 | 35 | 173 |
| TMT® 128 | 438.25 | 128.13 | 35 | 173 |
| TMT® 129 | 438.25 | 129.14 | 35 | 173 |
| TMT® 130 | 438.25 | 130.14 | 35 | 173 |
| TMT® 131 | 438.25 | 131.14 | 35 | 173 |
| Fragment 146 | 438.25 | 146.06 | 28 | 173 |

Processing of TSQ Vantage Data

Data was analysed in Skyline 3.1 (skyline.gs.washington.edu) using its small molecule capabilities. Fragment ion signals were used for identification verification. Peak integration of TMT® reporter channels was manually edited and areas were exported for further analysis.

Immunohistochemistry

For immunohistochemistry, the rabbit anti-TDO2A antibody (1:400) was used (20). Sections cut to 3 µm were incubated and processed with the TDO2 antibody using a Ventana BenchMark XT® immunostainer (Ventana Medical Systems, Tucson, Ariz., USA). The Ventana staining procedure included antigen-retrieval pretreatment with Ventana cell conditioner 1 (pH 8) for 1 h followed by incubation with the TDO2 antibody at 37° C. for 32 min. Incubation was followed by Ventana standard signal amplification, Ultra-Wash, counterstaining with hematoxylin and bluing reagent for 4 min. For visualization, the ultraView™ Universal FastRed Detection Kit (Ventana Medical Systems) was used.

Statistical Analysis

Data is expressed as mean Experiments were repeated at least three times with similar results. Analysis of significance was performed using the Student's t-test (SigmaPlot, Systat Software Inc., San Jose, Calif., USA).

Results

TMT®-Labelling of Tryptophan, 1-L-Methyl-Tryptophan, Kynurenine and Methyl-Kynurenine Labelling of the pure substances L-tryptophan, 1-L-methyl-tryptophan, L-kynurenine and methyl-kynurenine with TMT®-reagent resulted in HPLC retention time shifts, indicating that the analytes are successfully and completely labelled. MS measurements on a QTof II (Waters) instrument with direct infusion of varying amounts of TMT®-labelled L-tryptophan, 1-L-methyl-tryptophan, L-kynurenine and 1-L-methyl-kynurenine compared to unlabeled substances revealed that the TMT®-labelled analytes produced clearly higher signals than the unlabeled substances. The mass spectrometric response of TMT®-labelled tryptophan was more than 100-fold that of unlabeled tryptophan. 1-L-methyl-tryptophan and methyl-kynurenine produced a 200-fold higher MS-signal when labelled with TMT®-reagent, whereas for kynurenine the effect was lower with a more than two-fold higher signal. MS/MS-spectra showed that TMT®-reporter ion fragments are measureable and furthermore the signal intensities were clearly higher than for the structural fragments, proving that an efficient fragmentation is achieved and that the TMT®-reporter ions are ideal for quantitative purposes (data not shown).

Isobaric labelling enables multiplex measurement of tryptophan degradation in six cell culture supernatant samples in one experiment. SKOV-3 ovarian cancer cells constitutively degrade tryptophan to kynurenine in an IDO1-mediated fashion (10) and hence, they were used them as a model cell line to analyse the degradation of L- and D-tryptophan to kynurenine using a novel MS/MS-based TMT® sixplex approach.

Tryptophan and kynurenine concentrations in culture supernatants serve as a good readout for IDO1 activity of cells, and therefore SKOV-3 cell culture supernatant samples were used for the experiments. Each of six different SKOV-3 cell culture supernatant samples was labelled with one of six different TMT® sixplex reagents (Table 3).

TABLE 3

SKOV-3 cell culture supernatant samples labelling

| Sample | TMT® |
|---|---|
| 1 | 126 |
| 2 | 127 |
| 3 | 128 |
| 4 | 129 |
| 5 | 130 |
| 6 | 131 |

The six samples to be compared were mixed and subjected to HPLC/MS analysis, in which the analytes are separated by retention time and mass. Labelling of substances with TMT® sixplex reagents increases the monoisotopic mass [M+H] of tryptophan from 205.0969 to 434.2598 and of kynurenine from 209.0918 to 438.2547. MS/MS fragmentation of the labelled analytes (selected based on their exact masses) produces reporter ions that allow for relative quantitation of the analytes in each of the six samples. The identity of the analyzed MS signals was confirmed by the presence of substance-related fragments identical to the MS/MS spectra of the pure substances (data not shown).

Figure 2:
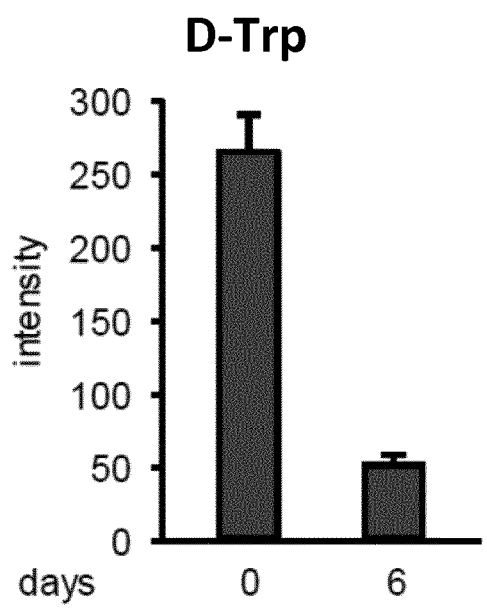
FIG. 2. Mean reporter ion intensities of three independent MS/MS reporter spectrum measurements of D-Trp (left) and Kyn (right) in cell culture media of SKOV-3 cells. The measured sample consists of six samples from three independent biological samples at different incubation times: day 0 (medium before contact with cells) and day 6 (upper panels) and days 0 to 5 (lower panels).
Figure 2:
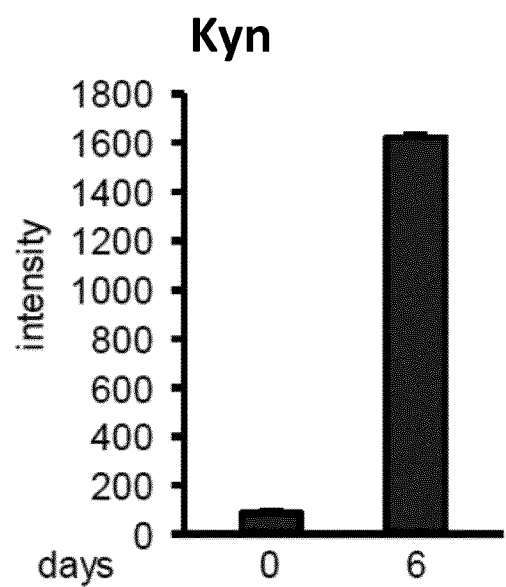
Figure 2:
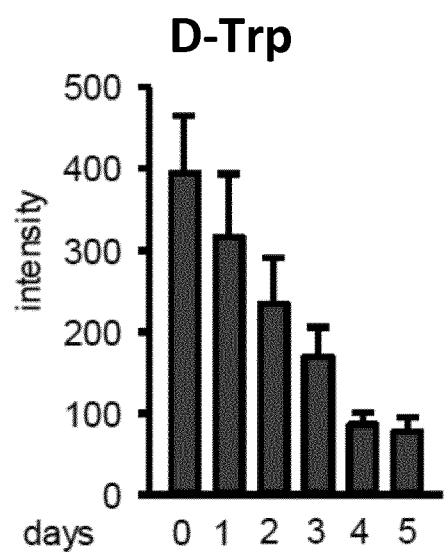
Figure 2:
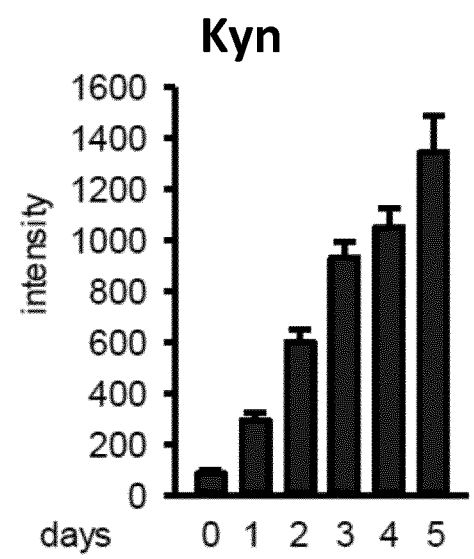

Tryptophan and kynurenine in cell culture supernatant of SKOV-3 cells were measured in TMT® sixplex mixtures of either three independent biological samples at day 0 (before contact with cells) and day 6 (day 0, day 6, day 0, day 6, day 0, day 6) or in time course experiments (day 0, 1, 2, 3, 4 and 5;). The results show that after 6 days of incubation, L-tryptophan was completely depleted from the media and a strong increase in kynurenine was observed (FIG. 1, top panels: L-tryptophan left and L-kynurenine right). Time course analysis revealed that L-tryptophan depletion from the media of SKOV-3 cells occurred between day 2 and 3 of incubation and maximal kynurenine concentrations were reached at day 3 (FIG. 1, bottom panels: L-tryptophan left and L-kynurenine right). In contrast, D-tryptophan was not entirely depleted from the media after 6 days of incubation (FIG. 2, top panels: D-tryptophan left and D-kynurenine right) and maximal concentrations of D-kynurenine were reached at day 5 (FIG. 2, bottom panels: D-tryptophan left and D-kynurenine right), reflecting slower degradation of D-tryptophan than L-tryptophan.

Multiplex Experiments Reveal that 1-MT is Degraded to Methyl-Kynurenine by Human Cancers Cells To study the dynamics of tryptophan degradation after treatment with the IDO inhibitor 1-L-MT, three independent biological samples of cell culture supernatants at day 0 and after 6 days of incubation of SKOV-3 cells with 1-L-MT were analyzed. Surprisingly, the supernatants of SKOV-3 cells that had been incubated with 1-L-MT yielded a peak at m/z 452.2706 Th. This mass corresponds to TMT® sixplex-labelled methyl-kynurenine.

This indicates that in analogy to the metabolism of tryptophan to kynurenine, 1-L-MT is metabolized to methyl-kynurenine. The presence of methyl-kynurenine was confirmed by the accurately measured exact mass, its retention time equal to the methyl-kynurenine standard and two fragments from the MS/MS spectra (data not shown). One of the fragments of methyl-kynurenine was observed at m/z 134.06 corresponding to a higher mass of 14 Th (inserted methylene group) compared to the known kynurenine fragment at m/z 120.04 Th. The second fragment was detected at m/z 160.07 Th corresponding to the peak at m/z 146.06 Th from kynurenine plus 14 Th from the inserted methylene group.

Figure 3:
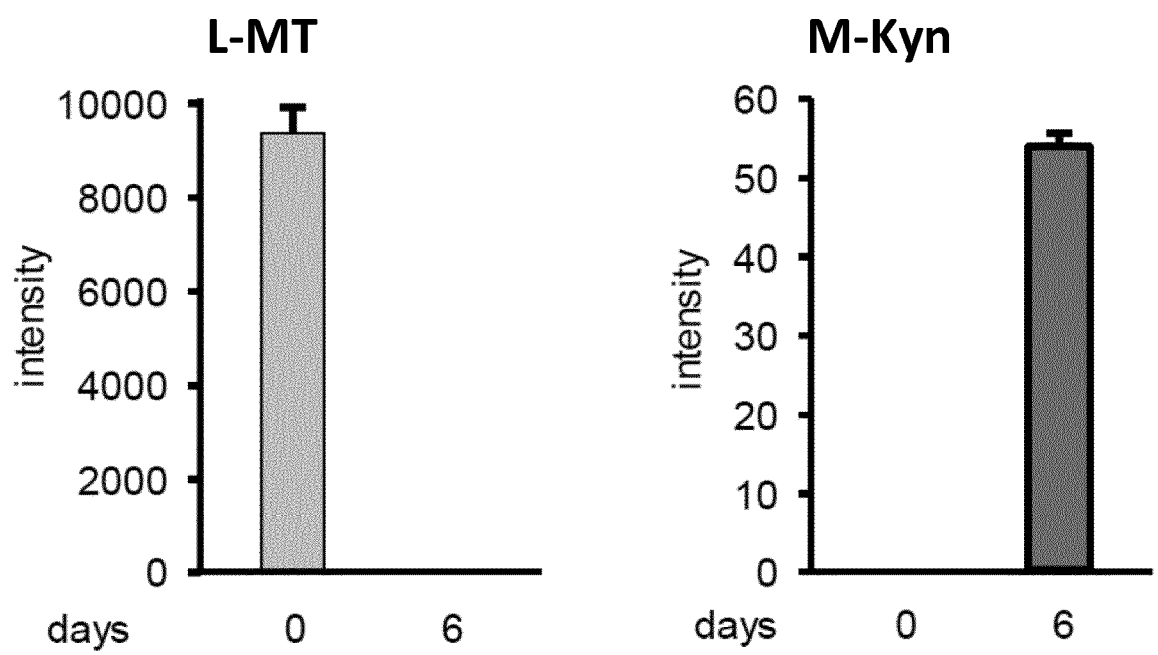
FIG. 3. Mean reporter ion intensities of HPLC-MS/MS-MS analysis of a TMT® sixplex labelled SKOV-3 cell culture supernatant sample mixture showing the metabolism of 1-L-methyl-tryptophan (L-MT) to Methyl-kynurenine (M-Kyn) in SKOV-3 cells. Six samples were used from three independent biological samples at different incubation times with L-MT: day 0 (medium before contact with cells) and day 6 (n=3).
Figure 4:
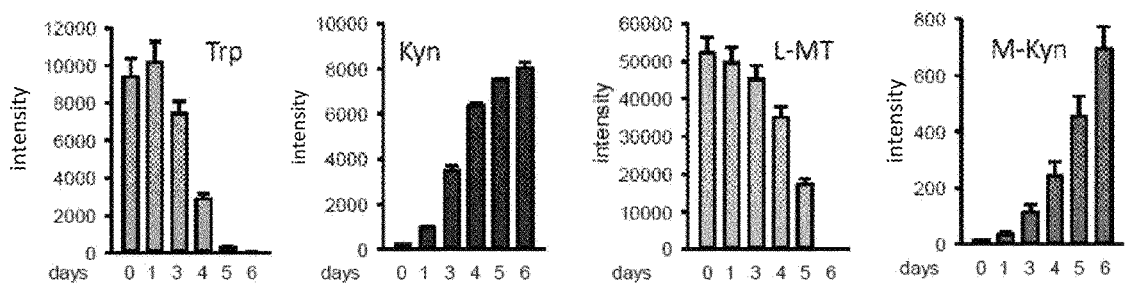
FIG. 4. Metabolism of 1-L-methyl-tryptophan (L-MT) and 1-D-methyl-tryptophan (D-MT) to Methyl-kynurenine (M-Kyn) in SKOV-3 cells. Mean reporter intensities of independent time course experiments of cell culture media of SKOV-3 cells incubated with 1000 µM 1-L-MT (upper panels) or 1000 µM 1-D-MT (lower panels) in the presence of 70 µM Trp. Mean intensities for Trp, Kyn, L-MT and M-Kyn (n=3) or Trp, Kyn, D-MT and M-Kyn (n=2) are shown.
Figure 4:
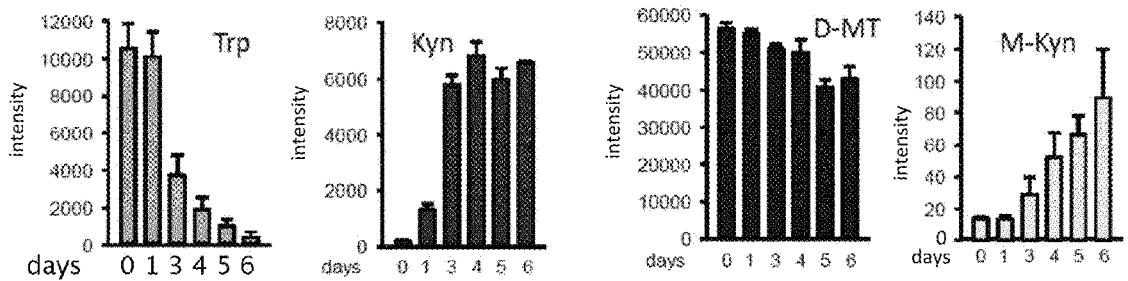
Figure 5:
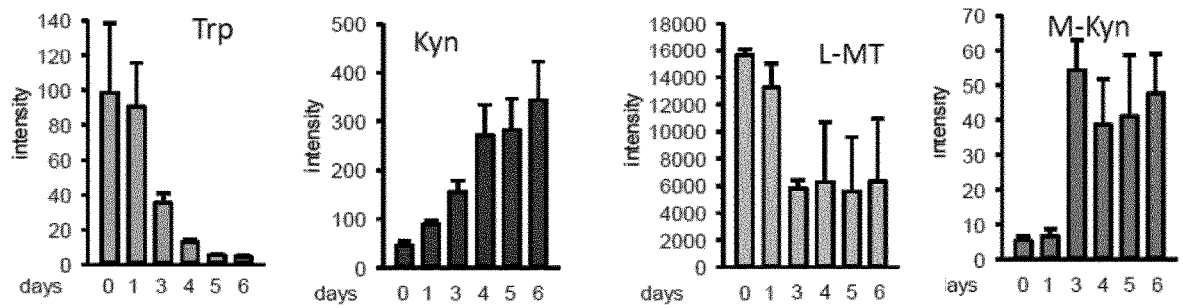
FIG. 5. Metabolism of 1-L-methyl-tryptophan (L-MT) and 1-D-methyl-tryptophan (D-MT) to Methyl-kynurenine (M-Kyn) in SKOV-3 cells. Mean reporter intensities of independent time course experiments of cell culture media of SKOV-3 cells incubated with 200 µM 1-L-MT (upper panels) or 200 µM 1-D-MT (lower panels) in the absence of exogenous tryptophan in addition to that contained in the serum: Mean intensities for Trp, Kyn, L-MT and M-Kyn are shown (n=3).
Figure 5:
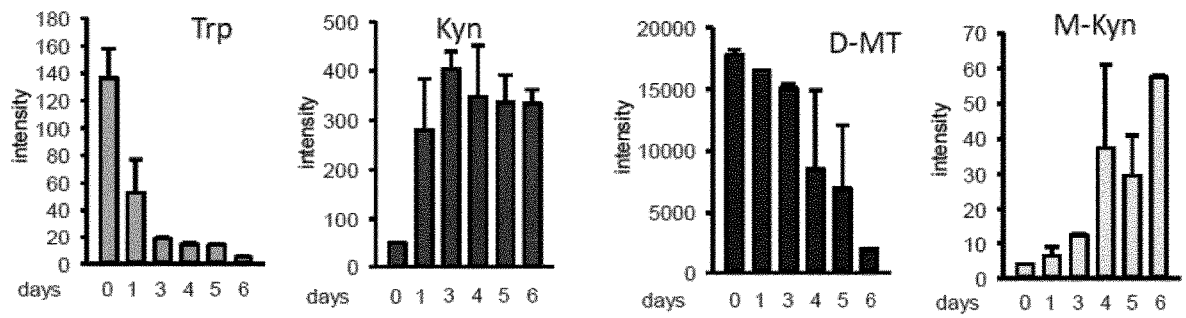

In the 6 days 1-L-MT was completely depleted from the cell culture media while in parallel a strong increase in methyl-kynurenine was observed (FIG. 3; left 1-L-MT, right M-Kyn). To further study the dynamics of the degradation of 1-MT time course analyses were performed with two different concentrations of 1-MT and tryptophan, respectively. Four different analytes, tryptophan, kynurenine, 1-MT and methyl-kynurenine were measured from cell culture supernatants of SKOV-3 cells at days 0, 1, 3, 4, 5 and 6 (FIGS. 4 and 5). The cells had been incubated with the L- or the D-enantiomer of 1-MT (1-L-MT or 1-D-MT) in order to gain information on putative differences in the metabolism of the two enantiomers of 1-MT. We analysed two different experimental setups: supernatants from cells treated with i) 1000 µM 1-MT with 70 µM tryptophan added to tryptophan-free medium (FIG. 4; upper panel 1-L-MT; lower panel 1-D-MT) and ii) 200 µM 1-MT with no tryptophan in addition to that present in the serum (FIG. 5; upper panel 1-L-MT; lower panel 1-D-MT). Both enantiomers of 1-MT were degraded to methyl-kynurenine, however, 1-L-MT was degraded more quickly than 1-D-MT and higher levels of methyl-kynurenine were reached (FIGS. 4 and 5). Tryptophan was metabolized to kynurenine more quickly and higher kynurenine levels were reached in the samples treated with D-MT than with L-MT (FIGS. 4 and 5). This may reflect a higher affinity of L-MT to the degrading enzyme than D-MT, causing a competitive substrate like tryptophan to be metabolised more quickly in D-MT samples.

Figure 6:
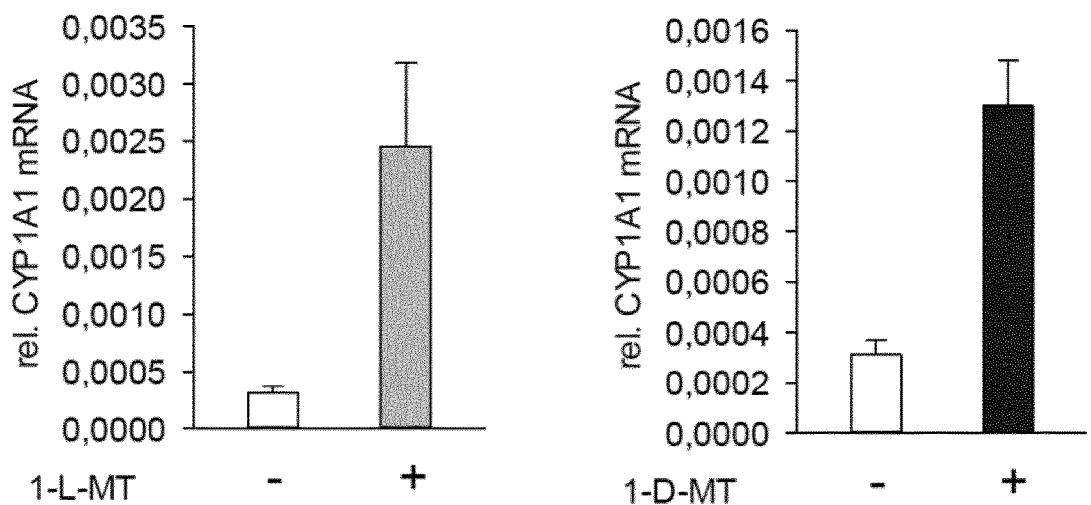
FIG. 6. Methyl-kynurenine activates the aryl hydrocarbon receptor. QRT-PCR analysis showing that treatment of SKOV-3 cells with 1-D/L-MT under tryptophan-free conditions induces the AHR target genes CYP1A1 (A) and TIPARP (B).
Figure 6:
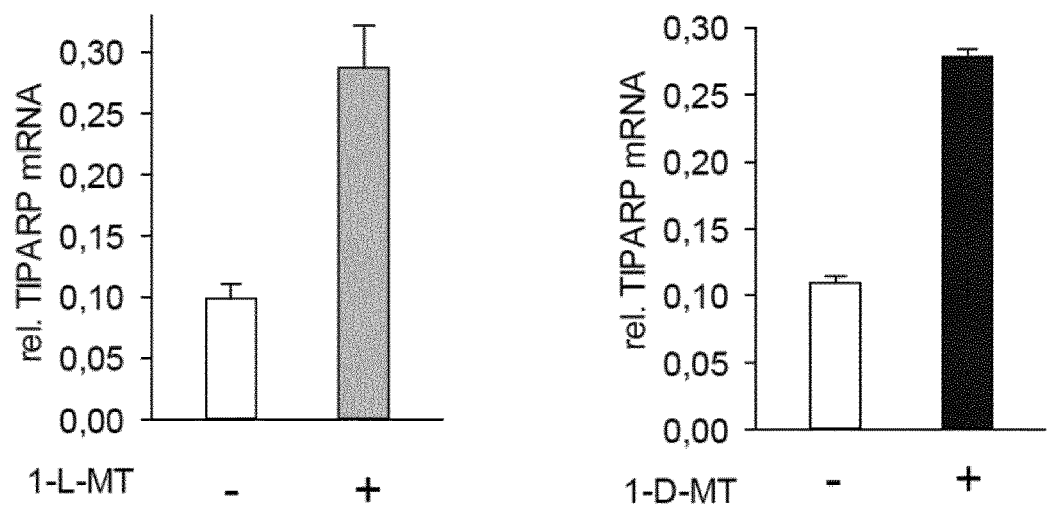

Kynurenine has been shown to suppress immune responses by activating the aryl hydrocarbon receptor (AHR)(3). Surprisingly, methyl-kynurenine generated by the degradation of 1-D/L-MT is capable of activating the AHR. Treatment of SKOV-3 cells with 1-D/L-MT under tryptophan-free conditions induced the AHR target genes CYP1A1 and TIPARP (FIGS. 6(A) and (B)), suggesting that methyl-kynurenine produced through degradation of 1-D/L-MT activates the AHR.

IDO is the Relevant Enzyme for the Degradation of 1-MT to Methyl-Kynurenine

Figure 7:
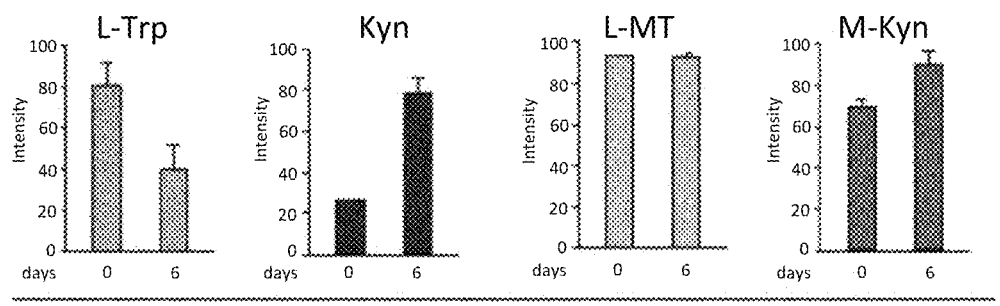
FIG. 7. HPLC-MS/MS-MS analysis of TMT® sixplex labelled cell culture supernatant from TDO2-expressing HEK cells after treatment with 1-L-MT (upper panel) or 1-D-MT (lower panel). Six samples were used from three independent biological samples at day 0 (medium before contact with cells) and after 6 days of incubation with 1-L-MT and 1-D-MT, respectively. Mean reporter intensities of independent experiments of cell culture supernatants incubated with L-MT or D-MT (n=3).
Figure 7:
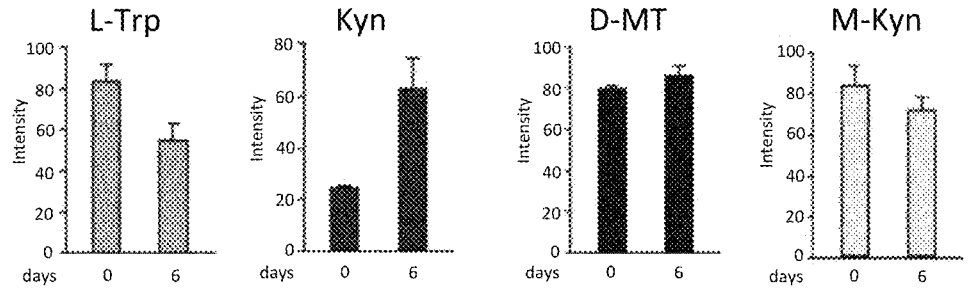

To analyze which enzyme degrades 1MT to methyl-kynurenine, we performed multiplex measurements of the supernatants of human embryonic kidney (HEK) cells that do not constitutively degrade tryptophan, and of HEK cells expressing either IDO or TDO. As expected HEK control cells (WT) degraded neither tryptophan nor 1-MT (data not shown). HEK cells expressing TDO degraded tryptophan to kynurenine, but no decrease of 1-MT was detected in the cell supernatants (FIG. 7; upper panels 1-L-TM, lower panel 1-D-TM). Only, a very slight increase in methyl-kynurenine was detected after treatment of the cells with 1-L-MT, but not 1-D-MT reflecting weak degradation of 1-L-MT, which was not detectable as a decrease of 1-L-MT due to relatively high amounts of the substrate.

Figure 8:
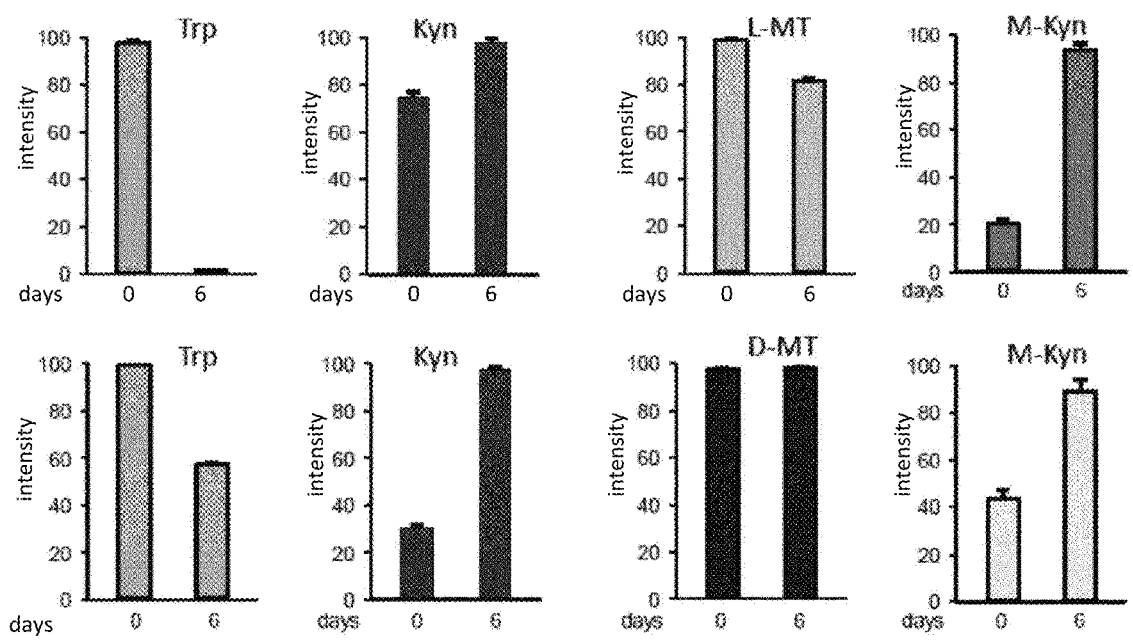
FIG. 8. IDO1 degrades 1-MT to methyl-kynurenine. Analysis of TMT® sixplex labelled supernatants of HEK cells overexpressing IDO1. Six samples were used from three independent biological samples after incubation with 1-L-MT (upper panels) or 1-D-MT (lower panels) at day 0 (medium before contact with cells) and day 6. Mean reporter intensities of independent experiments of cell culture supernatants incubated with L-MT or D-MT are shown (n=3).

In contrast, HEK cells expressing IDO produced methyl-kynurenine from both 1-L-MT (FIG. 8, upper panel) and 1-D-MT (FIG. 8, lower panel). In line with this, the amount of 1-L-MT slightly decreased, whilst a decrease of 1-D-MT was not detectable, possibly again due to the high amounts of the substrate. These data indicate that, while TDO-expressing cells may be capable of degrading minute amounts of 1-L-MT, IDO-expressing cells are able to degrade both enantiomers of 1-MT to methyl-kynurenine.

1-MT Degradation in Human Dendritic Cells

Figure 9:
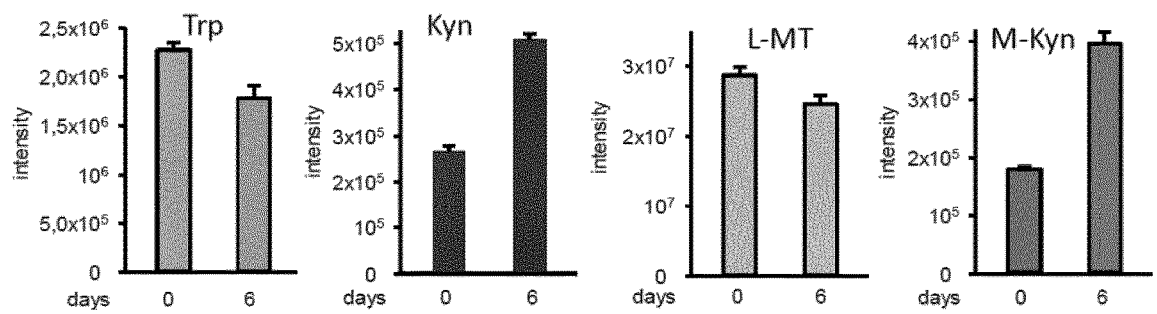
FIG. 9. 1-MT is also degraded by immune cells. Mean reporter intensities (B) of independent experiments of dendritic cell culture supernatants (from donor 1) incubated with L-MT (upper panels) or D-MT (lower panels) after stimulation with interferon gamma (1000 U/ml, n=3). Six samples were used from three independent biological samples at day 0 (medium before contact with cells) and after 6 days of incubation with L-MT or D-MT.
Figure 9:
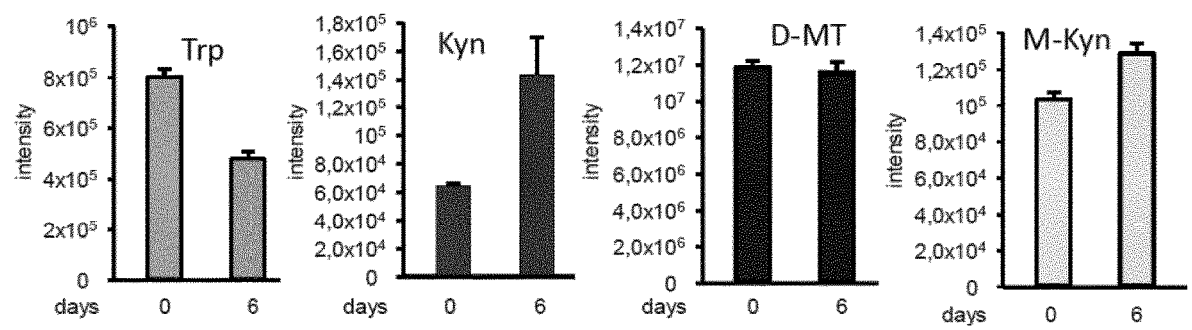

Immune cells can also express tryptophan-degrading enzymes and tryptophan degradation is known to exert potent immunosuppressive effects (9). To assess whether also immune cells, such as dendritic cells, degrade 1-MT to methyl-kynurenine, three independent biological samples of supernatants of human dendritic cells from two different donors were analysed (only donor 1 shown). Dendritic cells were stimulated with interferon-gamma (IFN γ) to induce IDO activity. We compared the three samples at day 0 and after 6 days of incubation with either 1-L-MT (FIG. 9 upper panels) or 1-D-MT (FIG. 9, lower panel). After 6 days of incubation a reduction of 1-L-MT and an increase in methyl-kynurenine were detected in the media of the dendritic cells from both donors (FIG. 9 upper panel), indicating that 1-L-MT is metabolized to methyl-kynurenine by human dendritic cells. Experiments with dendritic cells incubated with 1-D-MT showed an increase in methyl-kynurenine. However, no clear reduction of 1-D-MT levels was measured, possibly again due to relatively high amounts of the substrate (FIG. 9 lower panel). In summary, human dendritic cells metabolize 1-MT to methyl-kynurenine, with 1-L-MT being metabolized more efficiently than 1-D-MT.

Figure 10:
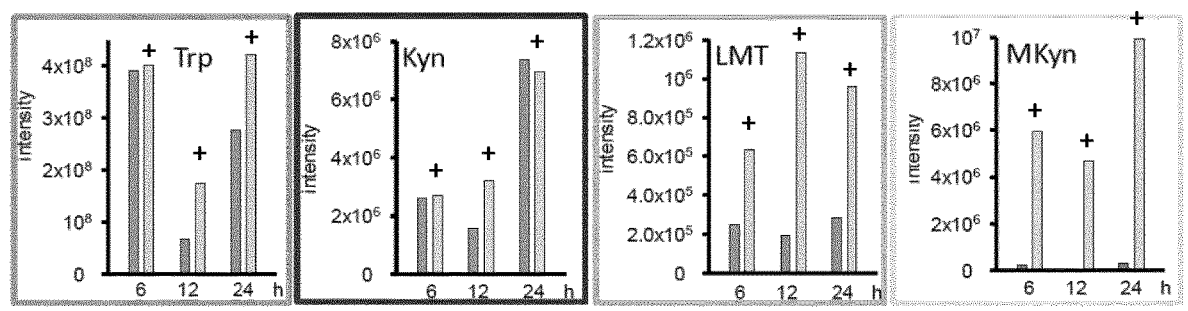
FIG. 10. 1-L-MT is degraded to methyl-kynurenine in a mouse model with inflammation-induced IDO expression. Relative abundances graphs of Trp, Kyn, 1-L-MT and Methyl-kyn showing the relative changes of the four selected analytes over time. "+": mice stimulated with LPS and injected with L-MT. Stimulation with LPS induced IDO as demonstrated by increasing Kyn production and reduction of trp. This stimulation also led to production of M-Kyn as indicated by higher reporter ions in mice stimulated with LPS and injected with L-MT.

Isobaric Labelling Enables the Detection of Methyl-Kynurenine in the Serum of Mice with Inflammation-Induced IDO Expression To explore whether the degradation of 1-MT also takes place in vivo, we analysed the sera of mice with LPS-induced IDO activity in the presence and absence of 1-L-MT. Two groups of mice were used and analysed at 3 different time points (6, 12 and 24 h after LPS administration). Both groups were stimulated with LPS to induce IDO activity. In addition, 1-L-MT was administered to the second group in order to assess the metabolism of 1-L-MT. LPS-stimulation appeared to successfully activate IDO in mice as treatment with LPS induced tryptophan degradation. Kynurenine levels in the mouse serum increased from 6 to 24 h after LPS administration (FIG. 10). Tryptophan concentrations were lowest 12 h after LPS administration. However, its concentration increased again at 24 h, possibly reflecting mechanisms counteracting systemic tryptophan depletion. The group of mice that had been injected with 1-L-MT (indicated by "+" in FIG. 10) displayed significantly higher 1-L-MT concentrations than the control group. The highest concentration of 1-L-MT was reached 24 h after administration, which may be due to slow absorption of 1-L-MT into the serum after intraperitoneal injection. In mice, in which IDO activity was induced by LPS and 1-L-MT was provided as a substrate, significantly higher concentrations of methyl-kynurenine were observed in comparison to mice treated with LPS alone, which suggests metabolism of 1-L-MT to methyl-kynurenine in vivo. Higher methyl-kynurenine concentrations were already measured at 6 h and increased further up to 12 h after injection of 1-L-MT.

Figure 11:
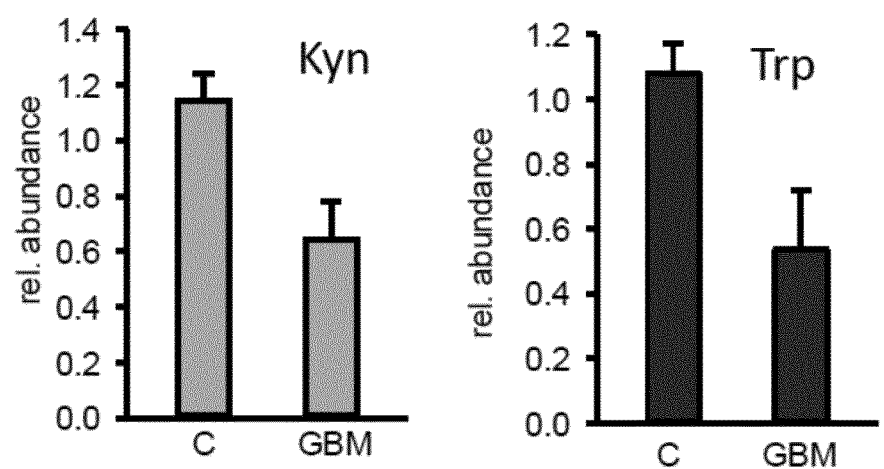
FIG. 11. Tryptophan and kynurenine are reduced in the serum of glioblastoma (GBM) patients. Relative abundance of kynurenine (left) and tryptophan (Trp) in the sera of healthy age- and sex-matched controls and glioblastoma patients measured on a Triple Quadrupole TSQ Vantage system. The abundances were calculated relative to a reference pool mixture consisting of equal volumes of the 4 sera of controls and the 4 glioblastoma patients.

Multiplex Analysis Reveals Reduced Tryptophan Serum Concentrations in Glioblastoma Patients Tryptophan metabolism is a target for cancer immunotherapy and clinical trials with IDO1 inhibitors are currently ongoing. Glioblastomas express high levels of the tryptophan degrading enzyme TDO, resulting in reduced serum tryptophan concentrations of these patients in comparison to healthy controls (3). Effective measurement of tryptophan and kynurenine levels in the blood is necessary to stratify patients to these treatments and to monitor treatment efficacy. In the present study, high expression of TDO2 was detected in the glioblastoma tissue of the patients from which sera were collected, suggesting that they would also show reduced serum tryptophan levels. The tryptophan and kynurenine abundance in the sera from four glioblastoma patients and four age- and sex-matched controls using two TMT® sixplex mixtures and a reference based design were compared. For this purpose a mixed reference sample was prepared that consisted of equal volumes of each individual sample. This reference sample enables comparison of all of the samples in the study. Each TMT® sixplex mixture contained the reference mixture, two sera from controls and two from glioblastoma patients. As triple quadrupole instruments are increasingly used in high-throughput and clinical settings, we established the multiplex measurement of tryptophan and kynurenine on a nLC II TSQ Vantage system. Tryptophan and kynurenine were measured from 0.1 µl serum-equivalent of the mixed sample, which corresponds to 0.017 µl of individual serum sample per measurement. Tryptophan and kynurenine levels were significantly reduced in the sera of glioblastoma patients compared to healthy age—and sex-matched controls (FIG. 11 showing the mean relative ratios calculated to the mixed reference sample of the analytes tryptophan and kynurenine in the two groups). The mean levels of tryptophan and kynurenine are reduced by a factor of 1.8 and 2, respectively. The good agreement with previous results (3) demonstrates that our setup is useful in measuring tryptophan and its metabolites in biological fluids such as serum.

SUMMARY OF RESULTS

The present inventors have demonstrated that both enantiomers of 1-MT are metabolized to methyl-kynurenine both in SKOV-3 cells as an example for cancer cells and also in dendritic cells as an example for cells of the immune system. Multiplex measurements suggest that IDO is able to catalyse the degradation of both enantiomers of 1-MT. TDO may be capable of degrading minute amounts of 1-L-MT, while degradation of 1-D-MT by TDO was not detectable. Multiplex measurements of mice sera demonstrate that methyl-kynurenine is also produced from 1 L-MT after LPS-stimulation in vivo. Experiments, in which SKOV-3 cells are treated with 1-MT, suggest that the product methyl-kynurenine activates the aryl hydrocarbon receptor and thus may suppress immune responses as has been shown for kynurenine (3). The formation of methyl-kynurenine may therefore counteract the inhibition of IDO by 1-MT, suggesting that other inhibitors, which are not themselves degraded to an aryl hydrocarbon receptor ligand, may be more efficient in mediating the desired effects.

Importantly, multiplex measurements of tryptophan in human serum samples have allowed comparison of serum tryptophan concentrations of glioblastoma patients with those of healthy controls. Glioblastomas are known to efficiently degrade tryptophan due to the expression of high levels of TDO, leading to reduction of serum tryptophan concentrations (3). Multiplex measurements revealed reduced tryptophan concentrations in the sera of glioblastoma patients, indicating that this method indeed is suitable for the measurement of tryptophan and kynurenine in human serum e.g. in clinical settings. While this reduction in serum tryptophan is not specific for glioblastomas as reduced tryptophan serum concentrations have been reported in a wide variety of conditions including diverse types of cancers, inflammatory and autoimmune diseases (9), it still may prove useful for stratification of patients to treatments with compounds modulating tryptophan degradation and monitoring of their efficacy.

REFERENCES

1. Hanahan D, and Weinberg R A. Hallmarks of cancer: the next generation. *Cell.* 2011; 144(5):646-74.
2. Muller A J, DuHadaway J B, Donover P S, Sutanto-Ward E, and Prendergast GC. Inhibition of indoleamine 2,3-dioxygenase, an immunoregulatory target of the cancer suppression gene Bin1, potentiates cancer chemotherapy. *Nat Med.* 2005; 11(3):312-9.
3. Opitz C A, Litzenburger U M, Sahm F, Ott M, Tritschler I, Trump S, Schumacher T, Jestaedt L, Schrenk D, Weller M, et al. An endogenous tumour-promoting ligand
4. Godin-Ethier J, Hanafi L A, Piccirillo C A, and Lapointe R. Indoleamine 2,3-dioxygenase expression in human cancers: clinical and immunologic perspectives. *Clin Cancer Res.* 2011; 17(22):6985-91.
5. Munn D H. Blocking IDO activity to enhance anti-tumor immunity. *Front Biosci (Elite Ed).* 2012; 4(734-45.
6. Opitz C A, Wick W, Steinman L, and Platten M. Tryptophan degradation in autoimmune diseases. *Cell Mol Life Sci.* 2007; 64(19-20):2542-63.
7. Bessede A, Gargaro M, Pallotta M T, Matino D, Servillo G, Brunacci C, Bicciato S, Mazza E M, Macchiarulo A, Vacca C, et al. Aryl hydrocarbon receptor control of a disease tolerance defence pathway. *Nature.* 2014; 511 (7508):184-90
8. Kaspar H, Dettmer K, Gronwald W, and Oefner P J. Advances in amino acid analysis. *Analytical and bioanalytical chemistry.* 2009; 393(2):445-52.
9. Murphy J P, Everley R A, Coloff J L, and Gygi S P. Combining amine metabolomics and quantitative proteomics of cancer cells using derivatization with isobaric tags. *Anal Chem.* 2014; 86(7):3585-93.
10. Opitz C A, Litzenburger U M, Opitz U, Sahm F, Ochs K, Lutz C, Wick W, and Platten M. The indoleamine-2,3-dioxygenase (IDO) inhibitor 1-methyl-D-tryptophan upregulates IDO1 in human cancer cells. *PloS one.* 2011; 6(5):e19823.
11. Badawy A A, and Morgan C J. Rapid Isocratic Liquid Chromatographic Separation and Quantification of Tryptophan and Six kynurenine Metabolites in Biological Samples with Ultraviolet and Fluorimetric Detection. *Int J Tryptophan Res.* 2010; 3(175-86.
12. Soto M E, Ares A M, Bernal J, Nozal M J, and Bernal J L. Simultaneous determination of tryptophan, kynurenine, kynurenic and xanthurenic acids in honey by liquid chromatography with diode array, fluorescence and tandem mass spectrometry detection. *J Chromatogr A.* 2011; 1218(42):7592-600.
13. Iizuka H, Ishii K, Hirasa Y, Kubo K, and Fukushima T. Fluorescence determination of D- and L-tryptophan concentrations in rat plasma following administration of tryptophan enantiomers using HPLC with pre-column derivatization. *J Chromatogr B Analyt Technol Biomed Life Sci.* 2011; 879(29):3208-13.
14. Lesniak W G, Jyoti A, Mishra M K, Louissaint N, Romero R, Chugani D C, Kannan S, and Kannan R M. Concurrent quantification of tryptophan and its major metabolites. *Analytical biochemistry.* 2013; 443(2):222-31.
15. Yamada K, Miyazaki T, Shibata T, Hara N, and Tsuchiya M. Simultaneous measurement of tryptophan and related compounds by liquid chromatography/electrospray ionization tandem mass spectrometry. *J Chromatogr B Analyt Technol Biomed Life Sci.* 2008; 867(1):57-61.
16. de Jong W H, Smit R, Bakker S J, de Vries E G, and Kema I P. Plasma tryptophan, kynurenine and 3-hydroxykynurenine measurement using automated on-line solid-phase extraction HPLC-tandem mass spectrometry. *J Chromatogr B Analyt Technol Biomed Life Sci.* 2009; 877(7):603-9.
17. Midttun O, Hustad S, and Ueland P M. Quantitative profiling of biomarkers related to B-vitamin status, tryptophan metabolism and inflammation in human plasma by liquid chromatography/tandem mass spectrometry. *Rapid Commun Mass Spectrom.* 2009; 23(9):1371-9.
18. Ohashi H, Iizuka H, Yoshihara S, Otani H, Kume M, Sadamoto K, Ichiba H, and Fukushima T. Determination of 1-tryptophan and 1-kynurenine in Human Serum by using LC-MS after Derivatization with (R)-DBD-PyNCS. *Int J Tryptophan Res.* 2013; 6(Suppl 1):9-14.
19. Carraro G, Albertin G, Forneris M, and Nussdorfer G G. Similar sequence-free amplification of human glyceraldehyde-3-phosphate dehydrogenase for real time RT-PCR applications. *Mol Cell Probes.* 2005; 19(3):181-6.
20. Miller C L, Llenos I C, Dulay J R, Barillo M M, Yolken R H, and Weis S. Expression of the kynurenine pathway enzyme tryptophan 2,3-dioxygenase is increased in the frontal cortex of individuals with schizophrenia. *Neurobiol Dis.* 2004; 15(3):618-29.

---

The invention claimed is:

1. A composition comprising tryptophan and one or more metabolites thereof, labelled with an amine-reactive mass tag that enhances signal intensity in mass spectrometry, wherein the tryptophan is at least one of L-tryptophan, D-tryptophan, 1-L-methyl-tryptophan, and 1-D-methyl tryptophan; and wherein the one or more metabolites of tryptophan is at least one of L-kynurenine, D-kynurenine, 1-L-methyl-kinurenine and 1-D-methyl-kinurenine.

2. The composition of claim 1, wherein the mass tag is an isobaric tag.

3. The composition of claim 1, wherein the mass tag is an isotopic mass tag.

4. The composition of claim 1, wherein the mass tag is a dimethylpiperidine-beta-alanine derivative comprising one or more heavy isotope substitutions of hydrogen, carbon, nitrogen and/or oxygen.

5. A method of measuring tryptophan and/or one or more metabolites thereof, wherein the method comprises: a) labelling one or more test samples with one or more mass tags; b) labelling purified or synthetic preparations of tryptophan and/or one or more metabolites thereof with one or more additional mass tags to form a reference sample, wherein the one or more additional mass tags are isobaric or isotopic variants of the same mass tags used in step a); c) mixing the one or more labelled test samples of step a) and the reference sample of step b) in a predefined ratio to form one or more analytical mixtures; d) analysing the one or more analytical mixtures by mass spectrometry, wherein the quantity of tryptophan and/or one or more metabolites thereof in the test samples is determined by comparing the signal intensity at the desired mass to charge ratio of the tryptophan and/or one or more metabolites thereof with the corresponding signal intensity at the mass to charge ratio of the tryptophan and/or the one or more metabolites thereof in the reference sample, wherein the tryptophan is at least one of L-tryptophan, D-tryptophan, 1-L-methyl-tryptophan, and 1-D-methyl tryptophan; and wherein the one or more metabolites of tryptophan is at least one of L-kynurenine, D-kynurenine, 1-L-methyl-kinurenine, and 1-D-methyl-kinurenine.

6. The method of claim 5, wherein the reference sample comprises the tryptophan and/or one or more metabolites thereof as defined in claim 1.

7. The method of claim 5, wherein the method is performed by Selected Reaction Monitoring using one or more transitions for the tryptophan and/or metabolites thereof, wherein the method comprises:
　i. comparing the amount of the tryptophan and/or metabolites thereof in said one or more test samples with amounts previously determined; or
　ii. comparing the ratios of the amounts of the tryptophan to the amounts of two or more metabolites of tryptophan in said one or more test samples;

wherein the method further comprises determining in said one or more test samples the rate and/or extent of tryptophan metabolism, wherein the transitions are defined in Table 1 and/or Table 2.

8. The method of claim 7, wherein step i) includes comparing the amounts of the tryptophan and/or metabolites thereof in said one or more test samples with known amounts of corresponding synthetic tryptophan and/or metabolites thereof which are identical to those present in said one or more test samples but have different isobaric or isotopic mass tags.

9. The method of claim 8, wherein the different mass tags are either different in structure or comprise different heavy isotope substitutions of hydrogen, carbon, nitrogen and/or oxygen.

10. A method of assaying for tryptophan and/or one or more metabolites thereof, wherein the method comprises: a) combining a test sample, comprising tryptophan and/or one or more metabolites thereof, with a calibration sample comprising at least two different aliquots of the tryptophan and/or one or more metabolites thereof, each aliquot of the calibration sample having a different known quantity of the tryptophan and/or one or more metabolites thereof, wherein the test sample and each aliquot of the calibration sample are differentially labelled with one or more isobaric mass labels, each with a mass spectrometrically distinct mass marker group, such that the test sample and each aliquot of the calibration sample can be distinguished by mass spectrometry; b) determining by mass spectrometry the quantity of the tryptophan and/or one or more metabolites thereof in the test sample and the quantity of the tryptophan and/or one or more metabolites thereof in each aliquot in the calibration sample, and calibrating the quantity of the tryptophan and/or one or more metabolites thereof in the test sample against the known and determined quantities of the tryptophan and/or one or more metabolites thereof in the aliquots in the calibration sample, wherein the tryptophan is at least one of L-tryptophan, D-tryptophan, 1-L-methyl-tryptophan, and 1-D-methyl tryptophan; and wherein the one or more metabolites of tryptophan is at least one of L-kynurenine, D-kynurenine, 1-L-methyl-kinurenine, and 1-D-methyl-kinurenine.

11. The method of claim 10, wherein the test sample comprises the tryptophan and one or more metabolites thereof and wherein a calibration sample is provided for the tryptophan and the one or more metabolites thereof, and wherein step (b) is repeated for the tryptophan and each of the one or more metabolites thereof.

12. The method of claim 10, wherein the method comprises a further step prior to step (a) of differentially labelling each test sample or each aliquot of the calibration sample with one or more isobaric mass labels, and of combining the differentially labelled aliquots to produce a calibration sample prior to step (a).

13. The method of monitoring the effectiveness of a treatment in a subject by measuring the levels of the tryptophan and/or one or more metabolites thereof according to claim 5.

14. The method of claim 13, wherein the treatment is a cancer treatment.

15. The method of stratifying subjects by measuring the levels of the tryptophan and/or one or more metabolites thereof according to claim 5.

16. The method of claim 15, wherein the subjects are stratified for a clinical trial.

17. The method of monitoring in a subject the recurrence of cancer after treatment by measuring the levels of the tryptophan and/or one or more metabolites thereof according to claim 5.

18. The method of claim 17, wherein the method is performed at intervals of 6 months or 3 months.

19. The method of diagnosing suppression of an immune response in a subject by measuring the levels of the tryptophan and/or one or more metabolites thereof according to claim 5.

20. The method of claim 19, wherein the suppression of the immune response is in a subject suffering from cancer.

21. The method of claim 13, wherein the subject is a human subject.

22. The method of claim 5, wherein the sample is selected from blood, plasma, serum, saliva, urine, tissue or a combination thereof.

23. The method according to claim 5, wherein the mass tag or mass label is an amine-reactive mass tag or mass label that enhances signal intensity in mass spectrometry.

24. An in vitro method for monitoring the effectiveness of a treatment in a subject, of stratifying subjects, of diagnosing suppression of an immune response in a subject, and/or of monitoring the recurrence of cancer in a subject, comprising measuring the level of the tryptophan and/or one or more metabolites thereof according to claim 1 in at least one sample obtained from the subject or the subjects, wherein the sample is selected from blood, plasma, serum, saliva, urine, tissue, or a combination thereof.

25. A kit comprising the composition of claim 1, wherein the kit further comprises one or more reagents to perform a method of measuring the tryptophan and/or one or more metabolites thereof.

* * * * *